United States Patent [19]

Sih

[11] Patent Number: 4,490,555
[45] Date of Patent: Dec. 25, 1984

[54] 9-SUBSTITUTED CARBACYCLIN ANALOGS

[75] Inventor: John C. Sih, Kalamazoo, Mich.

[73] Assignee: The Upjohn Company, Kalamazoo, Mich.

[21] Appl. No.: 360,090

[22] Filed: Mar. 19, 1982

[51] Int. Cl.³ .................... C07C 177/00; C07C 57/26
[52] U.S. Cl. .................... 562/501; 260/404;
260/404.5; 260/408; 260/410; 260/410.5;
260/410.9 R; 260/413; 260/464; 260/465 D;
260/465 F; 564/152; 564/158; 564/159;
564/172; 564/188; 564/428; 564/454; 564/427;
564/455; 564/466; 564/501; 564/87; 564/88;
564/89; 564/91; 564/96; 564/97; 564/98;
564/99; 560/12; 560/39; 560/45; 560/56;
560/119; 562/466; 562/455; 562/444; 562/427;
424/263; 424/275; 424/285; 424/305; 424/308;
424/317; 424/320; 424/321; 424/324; 424/325;
424/330; 424/343; 568/633; 568/734; 568/819;
542/421; 542/429; 549/79; 549/501
[58] Field of Search ............... 560/119, 12, 39, 45,
560/56; 562/501, 427, 444, 455, 466; 260/404,
404.5, 408, 410, 410.5, 410.9 R, 413, 464, 465 D,
465 F; 564/152, 158, 159, 172, 188, 428, 454,
427, 455, 466, 501, 87, 88, 89, 91, 96, 97, 98, 99;
568/633, 734, 819; 542/421, 429; 549/79, 501

[56] References Cited

U.S. PATENT DOCUMENTS

| 4,180,657 | 12/1979 | Sih ........................ 542/426 |
| 4,192,891 | 3/1980 | Haslanger ................. 424/305 |
| 4,225,508 | 9/1980 | Sih ..................... 260/346.22 |
| 4,238,414 | 12/1980 | Morton, Jr. .............. 564/453 |
| 4,306,075 | 12/1981 | Aristoff .................. 560/56 |
| 4,306,076 | 12/1981 | Nelson ................... 560/56 |

FOREIGN PATENT DOCUMENTS

| 2900352 | 7/1979 | Fed. Rep. of Germany . |
| 4024865 | 2/1979 | Japan . |
| 4063059 | 5/1979 | Japan . |
| 4063060 | 5/1979 | Japan . |
| 2012265 | 7/1979 | United Kingdom . |
| 2013661 | 8/1979 | United Kingdom . |
| 2017699 | 10/1979 | United Kingdom . |

OTHER PUBLICATIONS

Aristoff, P. A., J. Org. Chem. 46 (No. 9), 1981, pp. 1954–1957, "Practical Synthesis of 6a-Carbaprostaglandin I₂".
Barco, A., et al., J. Org. Chem. 45 (No. 23), 1980, pp. 4776–4778 "A New, Elegant Route to a Key Intermediate for the Synthesis of 9(O)-Methanoprostacyclin".
Hayashi, M., et al., Chem. Lett. 1979, pp. 1437–1440 "A Synthesis of 9(O)-Methanoprostacyclin".
Kojima, K., et al., Tetrahedron Lett. 39, 1978, pp. 3743–3746 "Total Synthesis of 9(O)-Methanoprostacyclin and Its Isomers".
Morton, D. R., Jr., et al., J. Org. Chem. 44 (No. 16), 1979, pp. 2880–2887 "Total Synthesis of 6a-Carbaprostaglandin I₂ and Related Isomers".
Nicolaou, K. C., et al., J.C.S. Chem. Comm., 1978, pp. 1067–1068 "Total Synthesis of Carboprostacyclin, a Stable and Biologically Active Analogue of Prostacyclin(PGI₂)".
Shibasaki, M., et al., Chem. Lett. 1979, pp. 1299–1300 "A Stereo and Regiospecific Route to the Synthetic Intermediate for the Synthesis of 9(O)-Methanoprostacyclin".
Shibasaki, M., et al., Tetrahedron Lett. 5, 1979, pp. 433–436 "New Synthetic Routes to 9(O)-Methanoprostacyclin. A Highly Stable and Biologically Potent Analog of Prostacyclin".
Skuballa, W., et al., Angew. Chem. 93 (No. 12), 1981, pp. 1080–1081, "Ein neuer Weg zu 6a-Carbacyclin—Synthese eines stabilen, biologisch potenten Prostacyclin-Analogons".
Sugie, A., et al., Tetrahedron Lett. 28, 1979, pp. 2607–2610 "Stereocontrolled Approaches to 9(O)-Methanoprostacyclin".
Yamazaki, M., et al., Chem. Lett. 1981, pp. 1245–1248 "1,2-Carbonyl Transposition of cis–Bicyclo[3.3.0]octan-2-one to Its 3-one Skeleton: Application to Syntheses of dl-Hirsutic Acid and dl-9(O)-Methanoprostacyclin".

Primary Examiner—Robert Gerstl
Attorney, Agent, or Firm—L. Ruth Hattan

[57] ABSTRACT

Novel compounds of the following general formula:

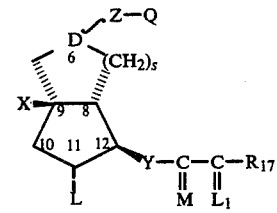

12 Claims, No Drawings

9-SUBSTITUTED CARBACYCLIN ANALOGS

BACKGROUND OF THE INVENTION

The present invention relates to novel compounds which are 9-substituted carbacyclin analogs, to processes for the preparation of said carbacyclin analogs and the use of said analogs as pharmacological agents or as intermediates for the preparation of compounds useful as pharmacological agents. This invention also relates to chemical intermediates for preparing the novel 9-substituted carbacyclin compounds described and claimed herein.

Prostacyclin is an endogenously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "$PGI_2$". Carbacyclin, 6a-carba-$PGI_2$, exhibits the structure and carbon atom numbering indicated in formula II when the C-5,6 positions are unsaturated. Likewise, for convenience, carbacyclin is referred to simply as "$CBA_2$".

A stable partially saturated derivative of $PGI_2$ is $PGI_1$ or 5,6-dihydro-$PGI_2$ when the C-5,6 positions are saturated, depicted with carbon atom numbering in formula I when the C-5,6 positions are saturated. The corresponding 5,6-dihydro-$CBA_2$ is $CBA_1$, depicted in formula II when the C-5,6 positions are saturated.

As is apparent from inspection of formulas I and II, prostacyclin and carbacyclin may be trivially named as derivatives of PGF-type compounds, e.g., $PGF_2\alpha$ of formula III. Accordingly, prostacyclin is trivially named 9-deoxy-6,9$\alpha$-epoxy-(5Z)-5,6-didehydro-$PGF_1$ and carbacyclin is named 9-deoxy-6,9$\alpha$-methano-(5Z)-5,6-didehydro-$PGF_1$. For description of prostacyclin and its structural identification, see Johnson, et al, Prostaglandins 12:915 (1976).

In naming the novel compounds of the present invention in general the art-recognized system of nomenclature described by N. A. Nelson, J. Med. Chem. 17:911 (1974) for prostaglandins is followed. As a matter of convenience, however, the novel carbacyclin derivatives herein are named as 6a-carba-prostaglandin $I_2$ compounds, or as $CBA_1$ or $CBA_2$ derivatives.

As used herein, broken line attachments to a ring, i.e., (- - -), indicate substituents in the "alpha" ($\alpha$) configuration, i.e., below the plane of said ring. Heavy solid line attachments to a ring, i.e., (—■), indicate substituents in the "beta" ($\beta$) configuration, i.e., above the plane of said ring. The use of wavy lines (~) herein will represent attachment of substituents in the alpha or beta configuration or attached in a mixture of alpha and beta configurations. Alternatively wavy lines will represent either an E or Z geometric isomeric configuration or the mixture thereof. Also, solid and dotted lines used together, as for example, in formulas I and II at C-5,6 positions indicates the presence of either a double bond or alternatively a single bond.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel carbacyclin analogs herein. Molecules of carbacyclin have several centers of asymmetry and therefore can exist in optically inactive form or in either of two enantiomeric (optically active) forms, i.e. the dextrorotatory and laveorotatory forms. The racemic form of carbacyclin contains equal numbers of both enantiomeric molecules. For convenience, reference to carbacyclin or $CBA_2$ or $CBA_1$ will refer to the optically active form thereof.

A formula as drawn herein which depicts a prostacyclin-type product or an intermediate useful in the preparation thereof, represents that particular stereoisomer of the prostacyclin-type product which is of the same relative stereochemical configuration as prostacyclin obtained from mammalian tissues or the particular stereoisomer of the intermediate which is useful in preparing the above stereoisomer of the prostacyclin type product. As drawn, formula I corresponds to that of $PGI_2$ endogenously produced in the mammalian species. In particular, refer to the stereochemical configuration at C-8 ($\alpha$, C-9 ($\alpha$), C-11 ($\alpha$) and C-12 ($\beta$) of endogenously produced prostacyclin. The mirror image of the above formula for prostacyclin represents the other enantiomer.

The term "prostacyclin analog" or "carbacyclin analog" represents that stereoisomer of a prostacyclin-type product which is of the same relative stereochemical configuration as prostacyclin obtained from mammalian tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia 63,059 and 63,060, also abstracted respectively as Derwent Farmdoc CPI Numbers 48154B/26 and 48155B/26. See also British published specifications 2,012,265 and German Offenlungsschrift 2,900,352, abstracted as Derwent Farmdoc CPI Number 54825B/30. See also British published applications 2,017,699 and 2,013,661 and U.S. Pat. No. 4,238,414. The synthesis of carbacyclin and related compounds is also reported in the chemical literature, as follows: Morton, D. R., et al, J. Org. Chem., 44:2880 (1979); Shibasaki, M., et al, Tetrahedron Lett., 433–436 (1979); Kojima, K., et al, Tetrahedron Lett., 3743–3746 (1978); Nicolaou, K. C., et al, J. Chem. Soc., Chemical Communications, 1067–1068 (1978); Sugie, A., et al, Tetrahedron Lett., 2607–2610 (1979); Shibasaki, M., Chem. Lett., 1299–1300 (1979), and Hayashi, M., Chem. Lett., 1437–40 (1979); Aristoff, P. A., J. Org. Chem. 46, 1954–1957 (1981); Yamazaki, M., et al, Chem. Lett., 1245–1248 (1981); and Barco, A., et al, J. Org. Chem. 45, 4776–4778 (1980); and Skuballa, W., et al, Angew. Chem., 93, 1080–1081 (1981). 7-Oxo and 7-hydroxy-$CBA_2$ compounds are apparently disclosed in U.S. Pat. No. 4,192,891. 19-Hydroxy-$CBA_2$ compounds are disclosed in U.S. Ser. No. 054,811, filed 5 July 1979. $CBA_2$ aroamtic esters are disclosed in U.S. Pat. No. 4,180,657. 11-Deoxy-$\Delta^{10}$- or $\Delta^{11}$-$CBA_2$ compounds are described in Japanese Kokai 77/24,865, published 24 February 1979. Related 9$\beta$-substituted compounds are disclosed in U.S. Pat. Nos. 4,306,075 and 4,306,076.

SUMMARY OF THE INVENTION

The present invention consists of compounds of formula IV wherein wherein X is chloro, iodo, or trifluoromethyl;
wherein D is cis—C=C($R_3$)—, trans—C=C($R_3$)— or >$CH_2CH_2$, wherein $R_3$ is hydrogen or fluoro;
wherein Z is:
(1) —$CH_2$—$(CH_2)_f$—$C(R_4)_2$— wherein each $R_4$ is the same and is hydrogen or fluoro, and f is zero, one, 2 or 3;
(2) trans—$CH_2$—CH=CH—; or
(3) —(Ph)—$(CH_2)_g$— wherein Ph is 1,2-, 1,3-, or 1,4-phenylene and g is zero, one, 2 or 3; with the proviso that when Z is —(Ph)—$(CH_2)_g$—, $R_3$ is hydrogen;
wherein Q is
(1) —$COOR_5$, wherein $R_5$ is
  (a) hydrogen,
  (b) ($C_1$-$C_{12}$)alkyl,
  (c) ($C_3$-$C_{10}$)cycloalkyl,
  (d) ($C_7$-$C_{12}$)aralkyl,
  (e) phenyl optionally substituted with one, 2 or 3 chloro or ($C_1$-$C_4$)alkyl,
  (f) phenyl substituted in the para-position with —$NHCOR_6$, —$COR_7$, —OC(O)$R_8$ or —CH=N—$NHCONH_2$, wherein $R_6$ is methyl, phenyl, acetamidophenyl, benzamidophenyl or —$NH_2$; $R_7$ is methyl, phenyl, —$NH_2$, or methoxy; and $R_8$ is phenyl or acetamidophenyl;
  (g) phthalidyl,
  (h) 3-(5,5-dimethyl-1,3,2-dioxaphosphorinan-2-yl)-2-oxopropan-1-yl P-oxide,
  (i) 3-(5,5-di(hydroxymethyl)-1,3,2-dioxaphosphorinan-2-yl)-2-oxopropan-1-yl P-oxide, or
  (j) a pharmacologically acceptable cation;
(2) —$CH_2OH$;
(3) —$COL_2$, wherein $L_2$ is
  (a) an amino group of the formula —$NR_9R_{10}$ wherein $R_9$ is hydrogen or ($C_1$-$C_{12}$)alkyl and $R_{10}$ is
    (i) hydrogen
    (ii) ($C_1$-$C_{12}$)alkyl
    (iii) ($C_3$-$C_{10}$)cycloalkyl,
    (iv) ($C_7$-$C_{12}$)aralkyl
    (v) phenyl optionally substituted with one, 2 or 3 chloro, ($C_1$-$C_3$)alkyl, hydroxy, carboxy, ($C_2$-$C_5$)alkoxycarbonyl, or nitro,
    (vi) ($C_2$-$C_5$)carboxyalkyl,
    (vii) ($C_2$-$C_5$)carbamoylalkyl,
    (viii) ($C_2$-$C_5$)cyanoalkyl,
    (ix) ($C_3$-$C_6$)acetylalkyl,
    (x) ($C_7$-$C_{12}$)benzoalkyl, optionally substituted by one, 2, or 3 chloro, ($C_1$-$C_3$)alkyl, hydroxy, ($C_1$-$C_3$)alkoxy, carboxy, ($C_2$-$C_5$)-alkoxycarbonyl, or nitro,
    (xi) pyridyl, optionally substituted by one, 2, or 3 chloro, ($C_1$-$C_3$)alkyl, or ($C_1$-$C_3$)alkoxy,
    (xii) ($C_6$-$C_9$)pyridylalkyl optionally substituted by one, 2, or 3 chloro, ($C_1$-$C_3$)alkyl, hydroxy, or ($C_1$-$C_3$)alkyl,
    (xiii) ($C_1$-$C_4$)hydroxyalkyl,
    (xiv) ($C_1$-$C_4$)dihydroxyalkyl,
    (xv) ($C_1$-$C_4$)trihydroxyalkyl;
  (b) cycloamine selected from the group consisting of pyrolidino, piperidino, morpholino, piperazino, hexamethyleneimino, pyrroline, or 3,4-didehydropiperidinyl optionally substituted by one or 2 ($C_1$-$C_{12}$)alkyl;
  (c) carbonylamino of the formula —$NR_{11}COR_{10}$, wherein $R_{11}$ is hydrogen or ($C_1$-$C_4$)alkyl and $R_{10}$ is other than hydrogen, but otherwise defined as above;
  (d) sulfonylamino of the formula —$NR_{11}SO_2R_{10}$, wherein $R_{11}$ and $R_{10}$ are defined in (c);
(4) —$CH_2NL_3L_4$, wherein $L_3$ and $L_4$ are hydrogen or ($C_1$-$C_4$)alkyl, being the same or different, or the pharmacologically acceptable acid addition salts thereof when Q is —$CH_2NL_3L_4$; or
(5) —CN;
wherein s is the integer one or 2;
wherein L is H,H; $\alpha$-$OR_{12}$,$\beta$-H; $\alpha$-H,$\beta$-$OR_{12}$; $\alpha$-$CH_2OR_{12}$,$\beta$-H; $\alpha$-H,$\beta$-$CH_2OR_{12}$ wherein $R_{12}$ is hydrogen or a hydroxyl protective group;
wherein Y is trans —CH=CH—, cis—CH=CH—, —$CH_2CH_2$—, or —C≡C—;
wherein M is $\alpha$-$OR_{12}$,$\beta$-$R_{14}$; or $\alpha$-$R_{14}$,$\beta$-$OR_{12}$, wherein $R_{12}$ is as defined above, and $R_{14}$ is hydrogen or methyl;
wherein $L_1$ is $\alpha$-$R_{15}$,$\beta$-$R_{16}$; $\alpha$-$R_{16}$,$\beta$-$R_{15}$; or a mixture thereof wherein $R_{15}$ and $R_{16}$ are hydrogen, methyl, or fluoro being the same or different with the proviso that one of $R_{15}$ and $R_{16}$ is fluoro only when the other of $R_{15}$ and $R_{16}$ is hydrogen or fluoro;
wherein $R_{17}$ is
(1) —$C_mH_{2m}CH_3$ wherein m is an integer of from one to 5,
(2) phenoxy optionally substituted by one, 2, or 3 chloro, fluoro, trifluoromethyl, ($C_1$-$C_3$)alkyl, or ($C_1$-$C_3$)alkoxy, with the proviso that not more than two substituents are other than alkyl and with the proviso that $R_{17}$ is phenoxy or substituted phenoxy, only when $R_{15}$ and $R_{16}$ are hydrogen or methyl, being the same or different;
(3) phenyl, benzyl, phenylethyl, or phenylpropyl optionally substituted on the aromatic ring by one, 2, or 3 chloro, fluoro, trifluoromethyl ($C_1$-$C_3$)alkyl, or ($C_1$-$C_3$)alkoxy, with the proviso that not more than two substituents are other than alkyl,
(4) cis—CH=CH—$CH_2CH_3$,
(5) —$(CH_2)_2$—CH(OH)—$CH_3$,
(6) —$(CH_2)_3$—CH=C$(CH_3)_2$,

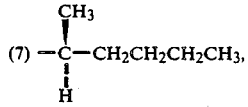

(7) $-\underset{H}{\overset{CH_3}{\underset{|}{\overset{|}{C}}}}-CH_2CH_2CH_2CH_3$,

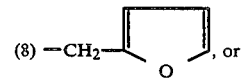

(8) —$CH_2$—[furan], or

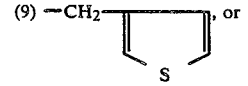

(9) —$CH_2$—[thiophene], or wherein $-\underset{L_1}{\overset{||}{C}}-R_{17}$ taken together is (1) ($C_4$-$C_7$)cycloalkyl optionally substituted by one to 3 ($C_1$-$C_5$)alkyl,
(2) 3-thienyloxymethyl, (3) 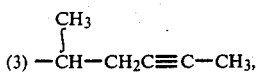

(4) $-C{\equiv}C-C_qH_{2q}CH_3$ wherein q is an integer of from 2 to 6, or (5) $-C_pH_{2p}CH{=}CH_2$ wherein p is an integer of from 3 to 7; and individual optical isomers thereof.

The compounds of Formulas V, IX and X, which are useful as intermediates in the preparation of the compounds of Formula IV, are also a part of the present invention. As used herein in the various Formulas the substituent groups or symbols $R_{17}$, $L_1$, Y, s, D, Z and X have the meanings defined in Formula IV. The groups $L_x$ and $M_x$ have the same meaning as defined for L and M in Formula IV only $R_{12}$ is other than hydrogen. $Z_1$ has the same meaning as Z only $Z_1$ is other than $-(P-h)-(CH_2)_q-$. The group $R_{21}$ is a silyl protecting group as defined hereinbelow.

DETAILED DESCRIPTION OF INVENTION

With regard to the divalent groups described above, i.e., M, L and $L_1$ said divalent groups are defined in terms of an α-substituent and a β-substituent which means that the α-substituent of the divalent group is in the alpha configuration with respect to the plane of the C-8 to C-12 cyclopentane ring and the β-substituent is in the beta configuration with respect to said cyclopentane ring.

The carbon atom content of various hydrocarbon containing groups is indicated by a prefix designating the minimum and maximum number of carbon atoms in the moiety. For example, in defining the moiety $L_2$ in the $-COL_2$ substituent group the definition $(C_1-C_{12})$alkyl means that $L_2$ can be an alkyl group having from one to 12 carbon atoms. Additionally, any moiety so defined includes straight chain or branched chain groups. Thus $(C_1-C_{12})$alkyl as set forth above includes straight or branched chain alkyl groups having from 1 to 12 carbon atoms and as additional illustration, when $L_2$ represents, for example, $(C_2-C_5)$carboxyalkyl, the alkyl moiety thereof contains from 1 to 4 carbon atoms and is a straight chain or a branched chain alkyl group.

The compounds of the present invention exhibiting the olefinic double bond at C-5,6 positions are $CBA_2$ compounds, while compounds which are saturated at the C-5,6 positions are $CBA_1$ compounds.

Novel compounds wherein Z is $-(Ph)-(CH_2)_g-$ are designated inter-o-, inter-m-, or inter-p-phenylene depending on whether the attachment between C-5 and the $-(CH_2)_g-$ moiety is ortho, meta, or para, respectively. For those compounds wherein g is zero, one or 2, the carbacyclin analogs so described are further characterized as 2,3,4-trinor-, 3,4-dinor-, or 4-nor, since in this event the Q-terminated side chain contains (not including the phenylene) 2, 3, or 4 carbon atoms, respectively, in place of the five carbon atoms contained in PGI$_2$. The missing carbon atom or atoms are considered to be at the C-4 to C-2 positions such that the phenylene is connected to the C-5 and C-1 to C-3 positions. Accordingly these compounds are named as 1,5-, 2,5-, and 3,5-inter-phenylene-CBA compounds when g is zero, one, or 2, respectively and when g is 3 the compounds are named as 4,5-interphenylene-CBA compounds.

Those CBA analogs wherein Z is $-CH_2-(CH_2)_f-C(R_4)_2-$ wherein $R_4$ is fluoro are characterized as "2,2-difluoro-" compounds. For those compounds wherein f is zero, 2, or 3, the carbacyclin analogs so described are further characterized as 2-nor, 2a-homo, or 2a,2b-dihomo, since in this event the Q-terminated side chain contains 4, 6, or 7 carbon atoms, respectively, in place of the five carbon atoms contained in PGI$_2$. The missing carbon atom is considered to be at the C-2 position such that the C-1 carbon atom is connected to the C-3 position. The additional carbon atom or atoms are considered as though they were inserted between the C-2 and C-3 positions. Accordingly these additional carbon atoms are referred to as C-2a and C-2b, counting from the C-2 to the C-3 position.

Those CBA analogs wherein Z is trans-$-CH_2-CH{=}CH-$ are described as "trans-2,3-didehydro-CBA" compounds.

Those novel compounds where s is 2 are further characterized as 7a-homo-CBA compounds by virtue of the cyclohexyl ring replacing the heterocyclic ring of prostacyclin.

Further, all of the novel compounds of the present invention contain a substituent at the 9β-position and are named as 9β-substituted compounds.

When $R_3$ is fluoro, "5-fluoro-" compounds are described.

When $R_{14}$ is methyl, the carbacyclin analogs are all named as "15-methyl-" compounds. Further, except for compounds wherein Y is cis-$-CH{=}CH-$, compounds wherein the M moiety contains an hydroxyl in the beta configuration are additionally named as "15-epi-" compounds.

For the compounds wherein Y is cis-$-CH{=}CH-$, the compounds wherein the M moiety contains an hydroxyl in the alpha configuration are named as "15-epi-CBA" compounds. For a description of this convention of nomenclature for identifying C-15 epimers, see U.S. Pat. No. 4,016,184, issued 5 Apr. 1977, particularly columns 24–27 thereof.

The novel carbacyclin analogs herein which contain $-(CH_2)_2-$, cis-$-CH{=}CH-$, or $-C{\equiv}C-$ as the Y moiety, are accordingly referred to as "13,14-dihydro, "cis-13", or "13,14-didehydro" compounds, respectively.

When $R_{17}$ is straight chained $-C_mH_{2m}-CH_3$, wherein m is an integer of from one to 5, the compounds so described are named as "19,20-dinor", "20-nor", "20-methyl" or "20-ethyl" compounds when m is one, 2, 4 or 5, respectively. When $R_{17}$ is branched chain $-C_mH_{2m}-CH_3$, then the compounds so described are "17-, 18-, 19-, or 20-alkyl" or "17,17-, 17,18-, -17,19-, 17,20-, 18,18-, 18,19-, 18,20-, 19,19-, or 19,20-dialkyl" compounds when m is 4 or 5 and the unbranched portion of the chain is at least n-butyl, e.g., 17,20-dimethyl" compounds are described when m is 5 (1-methylpentyl).

When $R_{17}$ is phenyl and neither $R_{15}$ nor $R_{16}$ is methyl, the compounds so described are named as "16-phenyl-17,18,19,20-tetranor" compounds. When $R_{17}$ is substituted phenyl, the corresponding compounds are named as "16-(substituted phenyl)-17,18,19,20-tetranor" compounds. When one and only one of $R_{15}$ and $R_{16}$ is methyl or both $R_{15}$ and $R_{16}$ are methyl, then the corresponding compounds wherein $R_{17}$ is as defined in this paragraph are named as "16-phenyl or 16-(substituted phenyl)-18,19,20-trinor" compounds or "16-methyl-16-phenyl- or 16-(substituted phenyl)-18,19,20-trinor" compounds respectively.

When $R_{17}$ is benzyl, the compounds so described are named as "17-phenyl-18,19,20-trinor" compounds.

When R$_{17}$ is substituted benzyl, the corresponding compounds are named as "17-(substituted phenyl)-18,19,20-trinor" compounds.

When R$_{17}$ is phenylethyl, the compounds so described are named as "18-phenyl-19,20-dinor" compounds. When R$_{17}$ is substituted phenylethyl, the corresponding compounds are named as "18-(substituted phenyl)-19,20-dinor" compounds.

When R$_{17}$ is phenylpropyl, the compounds so described are named as "19-phenyl-20-nor" compounds. When R$_{17}$ is substituted phenylpropyl the corresponding compounds are named as "19-(substituted phenyl)-20-nor" compounds.

When R$_{17}$ is phenoxy and neither R$_{15}$ nor R$_{16}$ is methyl, the compounds so described are named as "16-phenoxy-17,18,19,20-tetranor" compounds. When R$_{17}$ is substituted phenoxy, the corresponding compounds are named as "16-(substituted phenoxy)-17,18,19,20-tetranor" compounds. When one and only one of R$_{15}$ and R$_{16}$ is methyl or both R$_{15}$ and R$_{16}$ are methyl, then the corresponding compounds wherein R$_{17}$ is as defined in this paragraph are named as "16-phenoxy or 16-(substituted phenoxy)-18,19,20-trinor" compounds or "16-methyl-16-phenoxy- or 16-(substituted phenoxy)18,19,20-trinor" compounds, respectively.

When R$_{17}$ is cis—CH=CH—CH$_2$CH$_3$, the compounds so described are named as "cis-17,18-didehydro" compounds.

When R$_{17}$ is —(CH$_2$)$_2$—CH(OH)—CH$_3$, the compounds so described are named as "19-hydroxy" compounds.

When R$_{17}$ is —(CH$_2$)$_3$—CH=C(CH$_3$)$_2$, the compounds so described are named as "20-isopropylidene" compounds.

When R$_{17}$ is

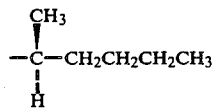

the compounds so described are named as 17(S),20-dimethyl compounds.

When R$_{17}$ is 2-furylmethyl or 3-thienylmethyl, i.e.,

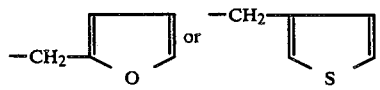

respectively the compounds so described are named as "17-(2-furyl)-18,19,20-trinor" compounds and "17-(3-thienyl)-18,19,20-trinor" compounds respectively.

When —C(L$_1$)—R$_{17}$ is

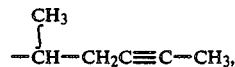

the compounds are named as "16-(R,S)methyl-18,19-tetradehydro" compounds.

When —C(L$_1$)—R$_{17}$ is optionally substituted cycloalkyl or 3-thienyloxymethyl, the compounds so described are named respectively 15-cycloalkyl-16,17,18,19,20-pentanor compounds and 16-(3-thienyl)oxy-17,18,19,20-tetranor compounds. The term 3-thienyloxymethyl means the moiety having the structure:

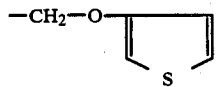

When —C(L$_1$)R$_{17}$ is —C≡C—C$_q$H$_{2q}$CH$_3$ wherein q is an integer of from 2 to 6 the compounds so described are named as "16,17-tetradehydro", "16,17-tetradehydro-20-methyl", "16,17-tetradehydro-20-ethyl", "16,17-tetrahydro-20-n-propyl" and "16,17-tetrahydro-20-n-butyl" compounds as the integer as represented by q varies from 2 to 6 respectively.

When —C(L$_1$)R$_{17}$ is —C$_p$H$_{2p}$CH=CH$_2$ wherein p is an integer of from 3 to 7 the compounds so described are named as "19,20-didehydro", "19,20-didehydro-18a,18b-dihomo", "19,20-didehydro-18a,18b,18c-trihomo", "19,20-didehydro-18a,18b,18c,18d-tetrahomo" compounds as the integer represented by p varies from 3 to 7 respectively.

When —C(L$_1$)R$_{17}$ is

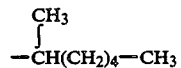

the compounds so described are named as "16(R,S),20-dimethyl" compounds.

When at least one of R$_{15}$ and R$_{16}$ is not hydrogen then (except for the 16-phenoxy or 16-phenyl compounds discussed above) there are described the "16-methyl" (one and only one of R$_{15}$ and R$_{16}$ is methyl), "16,16-dimethyl" (R$_{15}$ and R$_{16}$ are both methyl), "16-fluoro" (one and only one of R$_{15}$ and R$_{16}$ is fluoro), "16,16-difluoro" (R$_{15}$ and R$_{16}$ are both (fluoro) compounds. For those compounds wherein R$_{15}$ and R$_{16}$ are different, the carbacyclin analogs so represented contain an asymmetric carbon atom at C-16. Accordingly, two epimeric configurations are possible: "(16S)" and "(16R)". Further, there is described by this invention the C-16 epimeric mixture: "(16RS)".

When Q is —CH$_2$OH, the compounds so described are named as "2-decarboxy-2-hydroxymethyl" compounds.

When Q is —CH$_2$NL$_3$L$_4$, the compounds so described are named as "2-decarboxy-2-aminomethyl" or "2-(substituted amino)methyl" compounds.

When Q is —COL$_2$, the novel compounds herein are named as amides. Further, when Q is —COOR$_5$ and R$_5$ is other than hydrogen the novel compounds herein are named as esters and salts.

When Q is CN the novel compounds herein are named as 2-decarboxy-2-cyano compounds.

Examples of phenyl esters substituted in the para position (i.e., Q is —COOR$_5$, R$_5$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is —COL$_2$) include the following.

(1) Amides within the scope of alkylamino groups of the formula-NR$_9$R$_{10}$ are methylamide, ethylamide, p-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tert-butylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tertbutylcyclohexylamide, 3-isopropylcyclohexylamide, 2,2-dimethylcyclohexylamide, cycloheptylamide, cyclooctylamide, cyclonoylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N-benzyl-amide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutyalmide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxy-methyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula —$NR_{11}COR_{10}$ are methylcarbonylamide, ethylcarbonylamide, phenylcarbonylamide, and benzylcarbonylamide.

(4) Amides within the scope of sulfonylamino of the formula —$NR_{11}COR_{10}$ are methylsulfonylamide, ethylsufonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tert-butyl, isopentyl, neopentyl, butyl, pentyl, hexyl, heptyl, octyl, nonyl, decyl, undecyl, dodecyl, isomeric forms thereof.

Examples of $(C_3-C_{10})$cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tertbutylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of $(C_7-C_{12})$aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

Examples of $(C_4-C_7)$cycloalkyl optionally substituted by one to 3 $(C_1-C_5)$alkyl are cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, and cycloheptyl.

Examples of substituted phenoxy, phenyl, phenylmethyl, i.e., benzyl, phenylethyl, or phenylpropyl of the $R_{17}$ moiety are (o-, m-, or p-)tolyl, (o-, m-, or p-)ethylphenyl, 4-ethyl-o-tolyl, 5-ethyl-m-tolyl, (o-, m-, or p-)propylphenyl, 2-propyl-(m- or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(m- or p-)tolyl, 4-fluoro-2,5-xylyl, (2,4-, 2,5-, 2,6-, 3,4-, or 3,5-)difluorophenyl, (o-,m-, or p-)chlorophenyl, 2-chloro-p-tolyl, (3-, 4-, 5-, or 6L -)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 4-ethyl-o-tolyloxy, 5-ethyl-m-tolyloxy, (o-, m-, or p-)propylphenoxy, 2-propyl-(m- or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-fluoro-(m- or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3, 4, 5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenyl methyl, 4-ethyl-o-tolylmethyl, 5-ethyl-m-tolylmethyl, (o-, m-, or p-)propylphenylmethyl, 2-propyl-(m- or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(m- or p-)tolylmethyl, 4-fluoro-2,5-xylylmethyl, (2,4-, 2,5-, 2,6-, 3,4-, or 3,5-)difluorophenylmethyl, (o-, m-, or p-)tolylethyl, (o-, m-, or p-)ethylphenylethyl, 4-ethyl-o-tolylethyl, 5-ethyl-m-tolylethyl, (o-, m-, or p-)propylphenylethyl, 2-propyl-(m- or p-)tolylethyl, 4-isopropyl-2,6-xylylethyl, 3-propyl-4-ethylphenylethyl, (2,3,4-, 2,3,5-, 2,3,6-, or 2,4,5-)trimethylphenylethyl, (o-, m-, or p-)fluorophenylethyl, 2-fluoro-(m- or p-)tolylethyl, 4-fluoro-2,5-xylylethyl, (2,4-, 2,5-, 2,6-, 3,4-, or 3,5-)difluorophenylethyl, (o-, m-, or p-)chlorophenylmethyl, 2-chloro-p-tolylmethyl, (3, 4, 5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl, (o-, m-, or p-)chlorophenylpropyl, 2-chloro-p-tolylpropyl, (3, 4, 5, or 6-(chloro-o-tolylpropyl, 4-chloro-2-propylphenylpropyl, 2-isopropyl-4-chlorophenylpropyl, 4-chloro-3,5-xylylpropyl, (2,3-, 2,4-, 2,5-, 2,6-, 3,4-, or 3,5-)dichlorophenylpropyl, 4-chloro-3-fluorophenylpropyl, (3- or 4-)chloro-2-fluorophenylpropyl, (o-, m-, or p-)trifluoromethylphenylpropyl, (o-, m-, or p-)methoxyphenylpropyl), (o-, m-, or p-)ethoxyphenylpropyl, (4- or 5-)chloro-2-methoxyphenylpropyl, and 2,4-dichloro-(4- or 6-)methoxyphenylpropyl.

The group $—C_mH_{2m}CH_3$ wherein m is an integer of from one to 5 which $R_{17}$ may be represents straight or branched alkyl$C_1-C_5$ groups such as named hereinabove.

The terms phthalidyl; 3-(5,5-dimethyl-1,3,2-dioxaphosphorinan-2-yl)-2-oxopropan-1-yl P-oxide; and 3-(5,5-di(hydroxymethyl)-1,3,2-dioxaphosphorinan-2-yl)-2-oxopropan-1-yl P-oxide; which $R_5$ may represent in the $—COOR_5$ group mean the following respective moieties (a), (b) and (c):

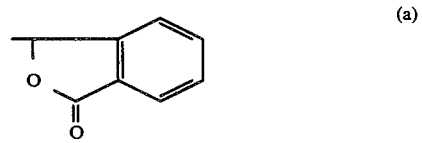

(a)

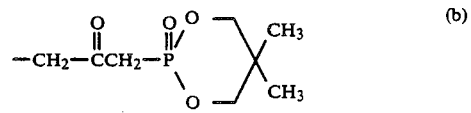

(b)

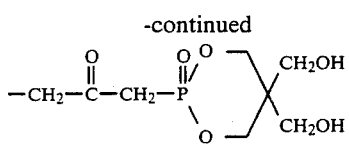

As indicated hereinabove $R_{12}$ is hydrogen or a protecting group. Those protective groups within the scope of $R_{12}$ are any group which replaces a hydroxy hydrogen and is neither attacked by nor is reactive to the reagents used in the transformations used herein as a hydroxy is and which is subsequently replaceable by hydrolysis with hydrogen in the preparation of the carbacyclin-type compounds. Several such protective groups are known in the art, e.g., tetrahydropyranyl and substituted tetrahydropyranyl. See for reference E. J. Corey, Proceedings of the Robert A. Welch Foundation, Conferences on Chemical Research, XII Organic Synthesis, pp. 51–79 (1969). Those blocking groups which have been found useful include:

(a) tetrahydropyranyl;
(b) tetrahydrofuranyl;
(c) a group of the formula $-C(OR_{24})(R_{18})-CH(R_{19})(R_{20})$, wherein $R_{24}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{18}$ and $R_{19}$ are alkyl of one to 4 carbon atoms, inclusive, phenyl, phenyl substituted with one, 2 or 3 alkyl of one to 4 carbon atoms, inclusive, or when $R_{18}$ and $R_{19}$ are taken together $-(CH_2)_a-$ or when $R_{18}$ and $R_{19}$ are taken together to form $-(CH_2)_b-O-(CH_2)_c$, wherein a is 3, 4, or 5 and b is one, 2, or 3, and c is one, 2, or 3, with the proviso that b plus c is 2, 3, or 4, with the further proviso that $R_{18}$ and $R_{19}$ may be the same or different, and wherein $R_{20}$ is hydrogen or phenyl; and
(d) silyl groups according to $R_{21}$, as qualified hereinafter.

When the protective group $R_{12}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the $R_{12}$ protective group is tetrahydrofuranyl, 2,3-dihydrofuran is used, as described in the preceding paragraph, in place of the 2,3-dihydropyran.

When the $R_{12}$ protective group is of the formula $-C(OR_{24})(R_{18})-CH(R_{19})(R_{20})$, wherein $R_{24}$, $R_{18}$, $R_{19}$, and $R_{20}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

$R_{21}$ is a silyl protective group of the formula $-Si(G_1)_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of $-Si(G_1)_3$ include trimethylsilyl, dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to $R_{12}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The protective groups as defined by $R_{12}$ are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

The compounds of Formula IV disclosed herein wherein $R_{12}$ is hydrogen produce certain prostacyclin-like pharmacological responses.

Accordingly, the novel formula IV compounds wherein $R_{12}$ is hydrogen are useful as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and additionally the compounds wherein s is one are useful as antithrombotic agents as indicated below.

(a) Platelet Aggregation Inhibition

The compounds of formula IV wherein $R_{12}$ is hydrogen, and s is one are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2–4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 μg per ml of whole blood. These compounds, i.e., the compounds of formula IV wherein $R_{12}$ is hydrogen, and s is one are useful in the treatment of peripheral vascular diseases, in the same manner as described in U.S. Pat. No. 4,103,026.

(b) Gastric Secretion Reduction

Compounds of Formula IV wherein $R_{12}$ is hydrogen are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 μg to about 20 μg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

Compounds of Formula IV wherein $R_{12}$ is hydrogen are also useful in reducing the undesirable gastrointestinal effects resulting from systemic administration of anti-inflammatory prostaglandin synthetase inhibitors, and are useful for that purpose by concomitant administration of said compounds of Formula IV and the anti-inflammatory prostagland in synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula IV compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formula IV wherein $R_{12}$ is hydrogen are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use Formula IV compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula IV compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When Q is $-COOR_5$, the novel Formula IV compounds so described are used for the purposes described above in the free acid form, in ester form, or in pharmacologically acceptable salt form. When the ester form is used, the ester is any of those within the above definition of $R_5$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula IV for the purposes described above are those with pharmacologically acceptable metal cations, ammonia, amine cations, or quaternary ammonium cations. Illustrative pharmacological acceptable cations which $R_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl) aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When Q is $-CH_2NL_3L_4$, the Formula IV compounds so described are used for the purposes described in either free base or pharmacologically acceptable acid addition salt form.

The acid addition salts of the 2-decarboxy-2-aminomethyl- or 2-(substituted aminomethyl)-Formula IV compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula IV with the stoichiometric amount of the acid corresponding to the pharmacologically acceptable acid addition salt.

The compounds of Formula IV wherein $R_{12}$ is a hydroxyl protecting group are useful as intermediates to the compounds of Formula IV wherein $R_{12}$ is hydrogen.

To obtain the optimum combination of biological response specificity, potency, and duration of activity, certain compounds within the scope of this invention are preferred. Preferred compounds of the present invention are the $CBA_2$ analogs, i.e., the compounds of Formula IV wherein the C-5,6 position is unsaturated, and of these compounds those wherein Y is $-CH_2CH_2-$, $-C\equiv C-$ or trans$-CH=CH-$ and/or Q is $-COOR_5$ or $-COL_2$ are preferred especially when $R_5$ is hydrogen, methyl, ethyl, or a pharmacologically acceptable cation such as sodium, and when each of $R_9$ and $R_{10}$ of the $L_2$ substituent moiety is hydrogen. Of these preferred compounds those wherein $R_3$ is hydrogen are more preferred. To further characterize the preferred embodiments of the present invention, compounds of Formula IV wherein $R_{17}$ is $-C_mH_{2m}CH_3$, benzyl, phenoxy, 3-thienylmethyl, or phenyl or wherein $-C(L_1)R_{17}$ taken together is cyclohexyl, 3-thienyloxymethyl or 3-ethylcyclobutyl, or $-CH(\sim CH_3)CH_2-/C=CCH_3$ are especially preferred. Also compounds wherein $R_{17}$ is $C_mH_{2m}CH_3$ and each of $R_{15}$ and $R_{16}$, which make up the $L_1$ substituent, are fluoro are especially preferred. Of all the preferred compounds described herein those compounds wherein X represents chloro are more particularly preferred.

Preferred for biological potency are formula IV $CBA_2$ analogs exhibiting the same C-5 isomeric configuration as $CBA_2$ itself. As is apparent from the foregoing as compounds satisfy more of the above preferences, said compounds are more preferred.

The carbacyclin analogs of the present invention as represented by Formula IV are prepared by various procedures as generally illustrated by the various charts provided herein.

As indicated hereinabove the hydroxyl groups at positions C-11 and C-15 of the compounds of the present invention may be protected by various groups generally employed in the art and protection of the hydroxyl functions and is generally desirable or necessary during the preparation of the compounds. Although any of the various protecting groups described herein may be employed those preferred are tetrahydropyranyl (THP) and tert-butyldimethylsilyl. Particularly, THP is a preferred protecting group during the various reactions required to add the side chains and t-butyldimethylsilyl is a preferred group to employ during separation of the isomers. Of course it may be useful or desirable to utilize protecting groups which may be selectively hydrolyzed. Also, when $R_{17}$ is $-(CH_2)_2CH(OH)-CH_3$ the hydroxyl group at C-19 generally is protected by the same type of groups utilized to protect the C-11 and C-15 hydroxyl groups during the preparation of said compounds and subsequently deprotected by hydrolysis as described herein.

Also, it will be apparent that in the preparation of the compounds the 5(E) and 5(Z) isomers generally may be separated when the C-11 and C-15 hydroxyl groups are either protected or are unprotected. However, it has been found that protection of these hydroxyl groups with, e.g., tert-butyldimethyl silyl often facilitates clean separation of the isomers in high yield. Separation of the 5(E) and 5(Z) isomers is achieved by conventional means, typically column chromatography is employed.

The compounds of Formula IV wherein Q is —COOR$_5$ wherein R$_5$ is a lower alkyl group are prepared from the compounds of Formula V wherein alkyl is, e.g., methyl or ethyl. The Formula IV compounds wherein X is iodo are prepared by treating an illuminated solution of a compound of Formula V and lead tetraacetate with iodine by the general procedure of D. H. R. Barton, et al., J. Chem. Soc. 2438 (1965). Suitable solvents for this reaction are inert solvents such as carbon tetrachloride or benzene and the reaction is carried out at reflux for about 30 minutes.

The compounds of Formula IV wherein X is chloro and Q is —COO lower alkyl are prepared using Grob's conditions (Synthesis 494 (1973) whereby a compound of Formula V is treated with N-chlorosuccinimide and lead tetraacetate in dimethylformamide-acetic acid at 45°-50° C. for 30 minutess under a nitrogen atmosphere.

The compounds of Formula IV wherein X is trifluoromethyl and Q is —COO lower alkyl are prepared by treating a compound of Formula V with sulfur tetrafluoride in methylene chloride and water by the general procedure of Rasmussen, et al., J. Org. Chem. 38, 3670 (1973) and references cited therein. The thus obtained compounds of Formula IV wherein Q is —COO lower alkyl are used to derive the remaining compounds of Formula IV wherein Q is other than —COO lower alkyl. The lower alkyl esters can be saponified by generally known procedures to the free C-1 carboxylic acids which can be used to derive other ester derivatives or amides as defined by Q is Formula IV. The amides also can be reduced to the amines using, e.g., lithium aluminum hydride as generally described in U.S. Pat. No. 4,073,808. The free C-1 acids or an ester thereof can be reduced to the corresponding C-1 alcohol by standard procedures, e.g., by refluxing with lithium aluminum hydride in an ether solvent. The thus obtained C-1 alcohol can be oxidized to the corresponding carboxaldehyde which upon treatment with a salt of hydroxylamine gives the oxime which upon dehydration gives the C-1 nitrile derivatives. All the aforementioned conversions are carried out by known procedures, see, e.g., the aforementioned British specifications which describe the synthesis of various carbacyclin compounds, and in particular G.B. Pat. No. 2,013,661.

Following the various C-1 conversions any protecting groups present at positions C-11, C-15, or C-19 are removed by hydrolysis or otherwise as described hereinabove.

The compounds of Formula V are prepared from the corresponding 9 —CH$_2$OH substituted compound, Formula VI, by oxidation using Jones reagent by generally known procedures.

The 9 —CH$_2$OH substituted compounds are prepared as depicted in Charts A, B, and C hereof. Referring to Chart A the enone (A-1) is subjected to photochemical addition of methanol by the procedure generally described by G. L. Bundy, Tetrahedron Lett. 1957 (1975) to give compounds of Formula A-2. The 9$\beta$—CH$_2$OH compounds of Formula A-2 are subjected to a Wittig reaction using an appropriate triphenylphosphorane of Formula A-3 by procedures known in the art to give A-4 compounds which is subsequently esterified by standard procedures, e.g., by treatment with acidic methanol. The compounds of Formula VI wherein D is —CH=C(~R$_3$) wherein R$_3$ is hydrogen and wherein Z is —(Ph)—(CH$_2$)$_q$— are prepared as depicted in Chart B. The ketones of Formula A-2 are reduced by conventional means using, for example, a borohydride reducing agent such as sodium, potassium or lithium borohydride, to the corresponding alcohol. The alcohol is converted to a sulfonate derivative, typically a methanesulfonate or toluenesulfonate by treatment with methanesulfonyl chloride or toluenesulfonyl chloride in the presence of a tertiary amine such as triethylamine. The sulfonate derivative is treated with sodium, lithium or potassium thiophenoxide to give the compounds of Formula B-1. The thiophenoxide is preferably prepared by reacting equal molar amounts of thiophenol and a base such as potassium tertiary butoxide just prior to reaction with the sulfonate. The compounds of Formula B-1 are oxidized to the corresponding phenylsulfonate using, e.g., m-chloroperbenzoic acid then treated with a strong base such as n-butyllithium to generate the corresponding anion. The anion is treated with an aldehyde of Formula B-2 and the resulting adduct is treated with acetic anhydride to give compounds of Formula B-3. The compounds of Formula B-3 are treated with sodium amalgam by procedures analogous to those described by P. J. Kocienski, et al., "Scope and Stereochemistry of an Olefin Synthesis from $\beta$-Hydroxysulphones", JCS Perkin I, 829-834 (1978) to give the olefins of Formula B-4. The various hydroxyl groups of B-4 are protected in such a manner to permit selective hydrolysis to give ultimately the 9$\beta$—CH$_2$OH compounds of Formula B-5 wherein the C-11, C-15, and C-19 hydroxyl groups which may be present are protected. For example, the 9$\beta$—CH$_2$OH group may be protected with, e.g., ethoxyethyl thus differentiating the primary alcohols. The R$_{21}$ silyl protecting group is conveniently removed via fluoride mediated hydrolysis using, e.g., tetrabutyl ammonium fluoride to give the C-1 position alcohol corresponding to Formula B-4 which is oxidized to the corresponding carboxylic acids, e.g., using Jones reagent and subsequently esterified by standard procedures, e.g., using acidic methanol after which the 9$\beta$-hydroxy protecting group is removed to give Formula B-5 compounds.

The compounds of Formula B-2 are prepared using known bis-acids of the formula

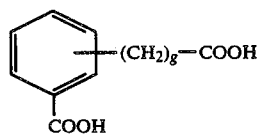

wherein g is zero, one, 2 or 3, which are reduced to the corresponding diol by conventional procedures, e.g., by using lithium aluminum hydride. About equal molar amounts of the diol and a silylating reagent of R$_{21}$ are combined thereby preferentially silylating the alkanol hydroxyl although some di-silylated compound is produced. The mono-silylated compounds of the formula

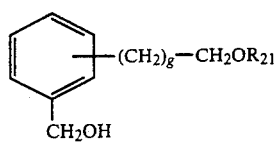

are oxidized to the aldehydes of Formula B-2 by conventional means, e.g., using manganese dioxide. See U.S. Pat. No. 4,306,075.

The compounds of Formula IV wherein D is $-CH=C(\sim R_3)$ and $R_3$ is fluoro are prepared by reacting compounds of Formula A-2 from Chart A hereof with a sulfoxime of the Formula C-1 as depicted in Chart C by the general procedures described in U.S. Pat. No. 4,238,414 at column 30, lines 36 to 62. The compounds of formula C-2 are then selectively hydrolyzed to the primary alcohol using, e.g., tetra-n-butylammonium fluoride. The alcohols thus obtained are oxidized to the corresponding carboxylic acids using, e.g., Jones reagent, which acids are subsequently esterified by generally known procedures to give compounds of Formula C-3.

The sulfoxime of Formula C-1 are prepared by treating a compound of the formula

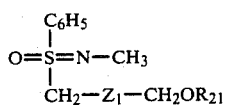

wherein $Z_1$ and $R_{21}$ have the meanings defined hereinabove, which compounds are known in the art (See U.S. Pat. No. 4,238,414) or are prepared by procedures generally known in the art with a strong base such as n-butyllithium in hexane to generate the anion which is treated with a fluorine source a preferred fluorine source being perchloryl fluoride, i.e., $FClO_3$.

The compounds of Formula IV wherein Q is —COOH can also be prepared utilizing a compound of Formula VII wherein W is —CHO by reacting said compound with the anion of an alkyl phosphonate of the formula

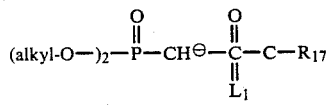

wherein alkyl is a lower alkyl such as methyl, ethyl, propyl or butyl and $R_{17}$ and $L_1$ have the meanings defined in Formula IV, under the conditions of a Wittig reaction to give a ketone intermediate corresponding to Formula VII wherein W is the group

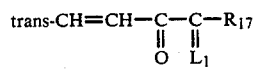

which is then reduced by hydride reduction to the α- or β-alcohol as defined by M in Formula IV to give compounds of Formula VII wherein W is the group

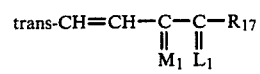

wherein $M_1$ is α—OH,β—H or α—H,β—OH and wherein $L_1$ and $R_{17}$ have the meanings defined in Formula IV. The thus obtained trans-vinyl compounds can be hydrogenated to give corresponding compounds of Formula VII wherein W is the group

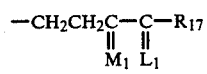

or can be halogenated followed by tetradehydrohalogenation to give the corresponding compounds of Formula VII wherein W is the group

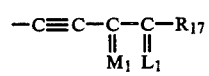

Hydrogenation of the thus obtained acetylene containing compounds with a Lindlar catalyst give the corresponding cis-vinyl compounds, i.e., Formula VII wherein W is the group

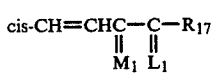

Once the appropriate transformations at the C-12 position are completed the C-11 protecting group is removed by hydrolysis to give the C-11 free hydroxyl compound, and the C-1 position carboxylic acid ester is hydrolyzed to the free acid by standard procedures known in the art.

The compounds of Formula IV wherein Q is —COOH are also prepared by treating a compound of Formula VII wherein W is —CHO with a phosphine of the formula $(alkyl)_3-P=CHCHO$ under the conditions of a Wittig reaction to give the corresponding compounds of Formula VII wherein W is trans-vinyl aldehyde group of the formula trans—$CH=CHCHO$ which is reduced to the corresponding trans-vinyl alcohol, i.e., Formula VII wherein W is trans—$CH=CHCH_2OH$. The trans-vinyl alcohol can be hydrogenated to give Formula VII compounds wherein W is the group —$CH_2CH_2CH_2OH$, or the trans-vinyl alcohol can be halogenated then tetradehydrohalogenated to give the corresponding acetylene alcohol, i.e., compounds of Formula VII wherein W is the group —$C\equiv CCH_2OH$. Hydrogenation of the acetylene alcohol with a Lindlar catalyst gives the corresponding cis-vinyl alcohols, i.e., Formula VII compounds wherein W is the group cis—$CH=CHCH_2OH$.

The thus obtained alcohols, i.e., compounds of Formula VII wherein W is trans—$CH=CHCH_2OH$, —$CH_2CH_2CH_2OH$, —$C\equiv CCH_2OH$ or cis—$CH=CHCH_2OH$ are oxidized to the corresponding aldehydes then treated with a Grignard reagent of the formula halo $MgCpH_2pCH=CH_2$, wherein halo is a halogen or an alkyl lithium of the formula $LiCpH_2pCH=CH_2$, or an acetylide anion of the formula —$C\equiv CCpH_2pCH_3$ or an anion of the formula

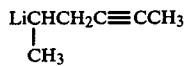

to give compounds of Formula VII wherein W is

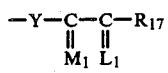

Formula W-6 wherein Y, $L_1$ and $R_{17}$ have the meanings defined in Formula IV and $M_1$ is $\alpha$—OH,$\beta$—H or $\alpha$—H,$\beta$—OH. The C-11 protecting group of the Formula A-6 compounds is then hydrolyzed to give the C-11 position free hydroxyl, and the C-1 position carboxylic acid ester is hydrolyzed to the corresponding free acid by standard procedures.

To prepare compounds of Formula IV wherein $R_{14}$ of the M substituent group is —$CH_3$ the corresponding C-15 alcohols are oxidized to the corresponding C-15 ketone then treated with methyl lithium or a methyl Grignard by procedures known in the art followed by hydrolysis of the C-11 protecting group and the C-1 ester to free acid.

The thus obtained C-1 carboxylic acid derivatives can be converted to the various other C-1 groups as represented by Q in Formula IV by the procedures described hereinbefore.

The compounds of Formula D are prepared by addition of the anion of a dialkyl methyl phosphonate of the formula

wherein alkyl is, e.g., methyl, ethyl, propyl or butyl with an ester of the formula

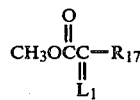

wherein $L_1$ and $R_{17}$ have the meanings defined in Formula IV by procedures well known in the art, followed by treatment with base (e.g., sodium hydride).

The compounds of Formula A-1 (Chart A) are prepared in a manner analogous to that described hereinabove for the preparation of Formula IV compounds from the compounds of Formula VII. By substituting a compound of Formula VIII wherein W is —CHO for the compound of Formula VII wherein W is —CHO in the aforedescribed procedure only leaving out the steps of removing hydroxyl protecting groups and ester hydrolysis one obtains the compounds corresponding to Formula VIII wherein W has the meaning depicted by the groups depicted as W-1 to W-6 hereinabove. Said Formula VIII compounds are converted to the compounds of Formula A-1 via the lactol and diketone phosphonate derivatives in a manner analogous to that described in U.S. Pat. No. 4,306,075 in reference to Chart A thereof.

The compounds of Formula VII wherein W is —CHO are prepared from the compounds of Formula IX by first removing the $R_{21}$ protecting group by acid or fluoride mediated hydrolysis to give the primary alcohol which is oxidized to the aldehyde of Formula VII by standard procedures, e.g., under the conditions of a Collins reaction.

The compounds of Formula IX are prepared from the corresponding compounds of Formula X in the same manner as described hereinbefore for the preparation of compounds of Formula IV wherein Q is —COO lower alkyl from compounds of Formula V.

The compounds of Formula X are prepared by oxidizing the corresponding compounds of Formula XI by generally known procedures, e.g., using Jones or Collins reagents.

The compounds of Formula XI are prepared from a compound of Formula XII which compounds are known in the art, see U.S. Pat. No. 4,306,075. By substituting a compound of Formula XII for compounds represented by Formula A-2 in each of Charts A, B and C hereof and following the general procedures described therein for the preparation of compounds of Formulas A-4, B-5 and C-3 one obtains the compounds of Formula XI wherein D is cis—C═C($R_3$)— or trans—C═C($R_3$)— which can be reduced to the corresponding compounds wherein D is —$CH_2CH_2$— by procedures generally known in the art, e.g., as generally described in British Published Application 2,017,699. For example, the reduction may be achieved by a standard hydrogenation in the presence of a catalyst such as palladium on charcoal or platinum dioxide in a lower alcohol such as ethanol or methanol.

A preferred method of preparing the compounds of Formula IV wherein Z is trans—$CH_2CH$═CH— is to utilize the appropriate intermediates of Formula IX wherein Z is —$CH_2$—$(CH_2)_f$—$C(R_4)_2$— and f is one and $R_4$ is hydrogen. Said Formula IX derivatives are treated with lithium amide base and phenylselenyl chloride to give the corresponding α-phenylselenyl derivatives which are reduced by, e.g., general procedures described in U.K. Application GB2,017,699 to give the 5,6-dihydro intermediates. The 5,6-dihydro intermediates are dehydrophenylselenized by treatment with hydrogen peroxide to give intermediates corresponding to Formula IX wherein Z is —$CH_2CH$═$CH_2$ and the carbon atoms at positions 5 and 6 are saturated, which intermediates can be converted to the corresponding derivatives wherein the terminal C-1 position corresponds to Q as defined herein by the general procedures described hereinabove.

When the alkyl ester has been obtained and an acid is desired, saponification procedures, as known in the art for PGF-type compounds are employed.

When an acid has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for alkyl, cycloalkyl or aralkyl esterification of the carboxy moiety of the acid compounds comprises transformation of the free acid to the corresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield the purity of product.

With regard to the preparation of the phenyl, particularly p-substituted phenyl esters disclosed herein (i.e., Q is —COOR$_5$ and R$_5$ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift 2,535,693, and Derwent Farmdoc No. 16828X.

The phthalidyl esters are obtained by treating the corresponding acid with a phthalidyl halide such as the bromide in, e.g., dimethylformamide in the presence of an amine base. The phosphoranyl esters are obtained by treating the corresponding acid with a 1-halo derivative, e.g., the 1-chloro derivatives of 3-(5,5-di(hydroxymethyl)-1,3,2-dioxaphosphorinan-2-yl)-2-oxopropan-1-yl P-oxide and 3-(5,5-dimethyl-1,3,2-dioxaphosphorinan-2-yl)-2-oxopropan-1-yl P-oxide in, e.g., acetonitrile in the presence of an organic amine.

Carboxyamides (Q is —COL$_2$) are prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the acids are prepared is, first, by transformation of such free acids to corresponding mixed acid anhydrides. By this procedure, the carbacyclin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at $-10°$ C. to $20°$ C.

Thereafter, the mixed anhydride is converted to the corresponding amido or cycloamido derivatives by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete.

Thereafter, the novel amido or cycloamido derivative is recovered from the reaction mixture by conventional techniques.

The carbonylamido and sulfonylamido derivative of the presently disclosed carbacyclin compounds are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure carbacyclin sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temperatures at or about $0°$ C. are employed.

The compounds of this invention prepared in free acid form are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation if inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

EXAMPLE 1

(5E,5Z)-9β-Carboxy-6a-carba-prostaglandin I$_2$ methyl ester, 11,15-bis-tetrahydropyranyl ether)

To a magnetically stirred solution of (5E,5Z)-9β-hydroxymethyl-6a-carba-prostaglandin I$_2$ methyl ester, 11,15-bis(tetrahydropyranyl ether) ((5.50 g, 9.79 mmol) in 160 ml of acetone, cooled in a −25° C. bath, is added over a 4 minute period 10.26 ml of Jones reagent (2.67M, 27.40 ml). Stirring is then maintained at −15° C. for one hour. The excess reagent is destroyed by addition of 7.5 ml of isopropanol and the reaction mixture stirred for 20 minutes. The contents are diluted with 800 ml of ethyl acetate, the ethyl acetate washed with saturated brine (3×150 ml), and dried through anhydrous sodium sulfate. Removal of the solvent in vacuo gives 6.90 g of a viscous oil. The crude product is chromatographed with 250 g of silica gel packed and eluted with ethyl acetate-Skellysolve B (3:7 containing 0.25% acetic acid) to yield 4.17 g of pure product as a viscous colorless oil.

NMR (CDCl$_3$,δ): 11.60 (broad s, 1H), 5.40 (m, 3H), 4.75 (m, 2H), 4.20–3.20 (m, 6H), 3.65 (s, 3H), 3.00–1.10 (m, 34H), 0.88 (t, 3H).

IR (cm$^{-1}$, neat): 3500–2800 (s), 1738 (s), 1700 (s), 1440 (m), 1200 (m), 980 (m).

EXAMPLE 2

(5E,5Z)-9β-Chloro-6a-carba-prostaglandin I$_2$ methyl ester, 11,15-bis-tetrahydropyranyl ether)

A mixture of (5E,5Z)-9β-carboxy-6a-carba-prostaglandin I$_2$ methyl ester, 11,15-bis (tetrahydropyranyl ether) (0.739 g, 1.28 mmol) and N-chlorosuccinimide (0.983 g, 7.36 mmol)is dissolved at room temperature with magnetic stirring in 10 ml of dimethylformamide-acetic acid (5:1, the solvent mixture is freed of oxygen by degassing with nitrogen prior to use). Oxygen is vigorously excluded from the reaction by bubbling nitrogen directly into the solution (18 gauge needle). Lead tetraacetate (0.567 g, 1.28 mmol) is added, the contents stirred at 25° C. for 2 to 3 minutes, the nitrogen needle removed, and the reaction flask placed in a 50° C. oil bath and heated for 20 minutes. The contents are allowed tocool to room temperature and diluted with 600 ml of ether. The ether solution is washed withwater, 5% sodium bicarbonate solution, saturated brine and dried through anhydrous sodium sulfate. Removal of the solvent in vacuo gives 0.838 g of a yellow oil. The crude product is chromatographed on 200 g of silica gel packed with Skellysolve B-ethyl sulfate (6:1). Taking 25 ml fractions, elution with the same solvent gives 0.403 g (fractions 30–46) of pure product (45% yield) as a viscous colorless oil.

NMR (CDCl$_3$,δ): 5.65–5.15 (m, 3H), 4.65 (m, 2H), 4.25–3.10 (m, 6H), 3.67 (s, 3H), 2.85–1.10 (m, 34H), 0.88 (t, 3H).

IR (neat, cm$^{-1}$): 2950 (s), 1735 (s), 1200 (m), 1020 (m, 975 (m).

EXAMPLE 3

(5E) and (5Z)-9β-Chloro-6a-carba-prostaglandin I$_2$

To a magnetically stirred solution of (5E,5Z)-9β-chloro-6-carbaprostaglandin I$_2$ methyl ester, 11,15-bis(tetrahydropyranyl ether) (0.403 g, 0.71 mmol) in 15 ml of methanol is added 2.40 ml (7.20 mmol) of 3N potassium hydroxide solution. Stirring is continued at 25° C. for 4 hours. The reaction is then diluted with water-crushed ice, acidified with 5.50 ml of 2N potassium hydrogen sulfate solution, and diluted with 300 ml of ether. The ether solution is washed with water, saturated brine and dried through sodium sulfate. Removal of the solvent gives 0.368 g (0.67 mmol) of the corresponding 11,15-bis(tetrahydropyranyl ether) free acid which is placed in acetic acid-water-tetrahydrofuran (20:10:3) and heated in a 56° C. oil bath for 3 hours. The solvents are removed in vacuo by azeotropic distillation with toluene to yield 0.323 g of crude product. This material is chromatographed with two Merck B Lobar columns connected in series. Taking 15 ml fractions, elution with chloroform-methanol-acetic acid (1000:40:5) yields 0.053 g (fractions 42–46) of the 5Z isomer and 0.156 g (fractions 48–62) of the 5E isomer.

TLC on silica gel in hexane-ethyl acetate (5:1, 1% acetic acid): methyl ester, R$_f$ 0.38; 11,15-bis(tetrahydropyranyl ether) free acid, R$_f$ 0.21; in chloroform-methanol-acetic acid (15:1:0.15) 5Z isomer, R$_f$0.37; 5E isomer, R$_f$0.34.

NMR (CDCl$_3$,δ) 11,15-bis(tetrahydropyranyl ether) free acid: 7.50 (broad s, 3H, OH's), 5.50 (m, 3H), 4.64 (m, 2H), 4.35–3.15 (m, 6H), 2.85–1.10 (m, 34H), 0.88 (t, 3H). 5Z isomer: 5.95 (broad s), 5.50 (m, 2H), 5.20 (m, 1H), 4.00 (m, 2H), 2.85–1.10 (m, 22H), 0.88 (t, 3H). 5E isomer: 5.95 (broad s, 3H, OH's), 5.50 (m, 2H), 5.25 (m, 1H), 4.00 (m, 2H), 2.80–1.10 (m, 22H), 0.88 (t, 3H).

IR (neat, cm$^{-1}$) (5Z and 5E isomers): 3600–3105 (broad s), 2940 (s), 1700 (s), 975 (m).

EXAMPLE 4

(5E,5Z)-9β-Chloro-6a-carba-prostaglandin I$_2$ methyl ester

Following the acid hydrolysis conditions described in Example 3 1.12 g (1.98 g) of (5E,5Z)-9β-chloro-6a-carba-prostaglandin I$_2$ methyl ester, 11,15-bis(tetrahydropyranyl ether) yields, after chromatography (60 g silica gel, ethyl acetate-Skellysolve B, 1:1), 0.520 g of the title compound. The products from the less polar column fractions are combined and resubjected to acid hydrolysis to yield, after silica chromatography, an additional 0.152 g of the title compound.

NMR (CDCl$_3$,δ): 5.50 (m, 2H), 5.25 (m, 1H), 4.00 (m, 2H), 3.67 (s, 3H), 3.5–3.00 (broad s, 2H, OH's), 2.90–1.10 (m, 22H), 0.88 (t, 3H).

IR (neat, cm$^{-1}$): 3400 (s), 2940 (s), 1740 (s), 1440 (s), 975 (m).

EXAMPLE 5

(5E)- and (5Z)-9β-Carboxy-6a-carba-prostaglandin I$_2$

A mixture of (5E,5Z)-9β-carboxy-6a-carba-prostaglandin I$_2$ methyl ester, 11,15-bis(tetrahydropyranyl ether) (0.12 g, 0.17 mmol), 4 ml of acetic acid, 2 ml of water and 0.60 of tetrahydrofuran is heated in a 45° C. oil bath for 2 hours. The solvents are removed in vacuo by azeotropic distillation with toluene to give 0.102 g of crude (5E,5Z)-9β-carboxy-6a-carba-prostaglandin I$_2$ methyl ester dissolved in 3.50 ml of methanol, treated with 0.63 ml of 3N potassium hydroxide and magnetically stirred at 25° C. for 2 hours. The reaction solution is then treated with 4 ml of 2N potassium hydrogen sulfate, 10 ml of saturated brine and extracted with ethyl acetate. The ethyl acetate extract is washed with saturated brine and dried through anhydrous sodium sulfate. Removal of the solvent in vacuo affords 95 mg of crude product which is chromatographed on two Merck A Lobar columns connected in series. Elution with acetone-methylene chloride (2:3 containing 0.25% acetic acid) gives 11.5 mg of the 5E isomer, 14 mg of a mixture of 5E and 5Z isomers, and 28.0 mg of the 5Z isomer.

TLC on silica gel in acetone-methylene chloride (1:2, 1% acetic acid), (5E,5Z)-9β-carboxy-6a-carba-prostaglandin I$_2$ methyl ester: R$_f$ 0.19; in methylene chloride-methanol-acetic acid (9:1:0.1), 5E isomer: R$_f$ 0.36; 5Z isomer: R$_f$ 0.33.

NMR (CDCl$_3$,δ), (5E,5Z)-9β-carboxy-6a-carba-prostaglandin I$_2$ methyl ester: 5.53 (m, 2H), 5.25 (m, 1H), 4.30 (broad s, 3H, OH's), 4.00 (m, 2H), 3.67 (s, 34), 2.95–1.10 (m, 22H), 0.88 (t, 3H); (CD$_3$OD,δ), 5Z isomer: 5.50 (m, 2H), 5.25 (m, 1H), 3.85 (m, 2H), 3.10–1.10 (m, 22H), 0.88 (t, 3H).

EXAMPLE 6

(5E,5Z)-9β-Iodo-6a-carba-prostaglandin I$_2$ methyl ester, 11,15-bis(tetrahydropyranyl ether)

To a magnetically stirred solution (5E,5Z)-9β-carboxy-6a-carbaprostaglandin I$_2$ methyl ester, 11,15-bis(tetrahydropyranyl ether) (0.359 g, 0.62 mmol) in 14 ml of carbon tetrachloride is added in one portion 0.337 g (0.76 mmol) of lead tetraacetate. The reaction is freed of oxygen by bubbling nitrogen directly into the solution (18 gauge needle) for 5 minutes. The nitrogen needle is removed and the reaction flask (fitted with condenser and nitrogen inlet) is placed in an oil bath maintained at 65° C. The contents are stirred for 17 minutes after which the oil bath temperature is raised to 80°–85° C. and a solution of iodine (0.185 g, 0.73 mmol) in 40 ml of carbon tetrachloride is added over a 15 minute period to the yellow colored solution. During the iodine addition, the reaction vessel is irradiated using a 300-watt Tungsten lamp. After addition, stirring and irradiation is maintained at 80°–85° C. for an additional 10 minutes. The contents are allowed to cool to room temperature and diluted with 400 ml of chloroform solution is successively washed with 15% sodium thiosulfate solution (3×100 ml), water, saturated brine and dried through sodium sulfate. Removal of the solvent in vacuo gives 0.466 g of crude product which is chromatographed on an 11×300 mm Michel-Miller column dry packed with HPLC grade silica gel. Taking 15 ml fractions, elution with Skellysolve B-ethyl acetate (10:1) yields 0.175 g (fractions 17–27) of the title compound.

NMR (CDCl$_3$,δ): 5.60–5.10 (m, 3H), 4.60 (m, 2H), 4.25–3.10 (m, 6H), 3.66 (s, 3H), 3.00–1.10 (m, 34H), 0.88 (t, 3H).

EXAMPLE 7

(5E,5Z)-9β-Iodo-6a-carba-prostaglandin I$_2$ methyl ester

A solution of (5E,5Z)-9β-iodo-6a-carba-prostaglandin I$_2$ methyl ester, 11,15-bis(tetrahydropyranyl ether) (0.175 g, 0.27 mmol) in 8.50 ml of acetic acid-water-tetrahydrofuran (20:10:3) is heated in a 45° C. oil bath for 2 hours. The solvents are removed in vacuo by azeotropic distillation with benzene to give 0.176 g of an oil which is diluted with 300 ml of hexane-ethyl acetate (60:40) and successively washed with saturated brine (3×60 ml), 5% sodium bicarbonate (2×75 ml), saturated brine and dried through anhydrous sodium sulfate. Removal of the solvent in vacuo gives 0.133 g of crude product which is chromatographed on an 11×300 mm Michel-Miller column dry packed with HPLC grade silica gel. Taking 15 ml fractions, elution with ethyl acetate-Skellysolve B (1.5:1) yields 0.085 g (fractions 28–62) of the title product, a viscous oil, as a mixture of 5E and 5Z isomers.

NMR (CDCl$_3$,δ): 5.45 (m, 2H), 5.22 (m, 1H), 4.00 (m, 2H), 3.67 (s, 3H), 3.50 (broad s, 2H, OH's), 3.00–1.10 (m, 22H), 0.88 (t, 3H).

IR (neat, cm$^{-1}$): 3350 (s), 2920 (s), 1738 (s), 1440 (m), 975 (m).

EXAMPLE 8

(5E,5Z)-9β-Iodo-6a-carba-prostaglandin I$_2$

To a magnetically stirred solution of (5E,5Z)-9β-iodo-6a-carbaprostaglandin I$_2$ methyl ester (0.054 g, 0.11 mmol) in 0.60 ml of methanol is added 0.34 ml of 3N potassium hydroxide solution. Stirring is continued at 25° C. for 1.5 hours. The solution is diluted with 4 ml of ice water, acidified with 0.60 ml of 2N potassium hydrogen sulfate solution and extracted with ethyl acetate. The ethyl acetate solution is washed with saturated sodium sulfate and dried through anhydrous sodium sulfate. Removal of the solvent in vacuo affords 0.043 g of an oil which is chromatographed with two Merck B Lobar columns connected in series. Taking 15 ml fractions, elution with chloroform-methanolacetic acid (1000:40:5) gives 0.030 g of a 4 component mixture. TLC on silica gel analysis (chloroform-methanol-acetic acid, 15:1:0.15) indicates two UV positive products [R$_f$ 0.30 (35%); R$_f$ 0.28 (35%)] and two non-UV products [R$_f$ 0.31 (5–10%); R$_f$ 0.29 (20%)]. The $^1$H NMR (d$_4$-methanol) spectrum of this mixture shows a multiplet at δ 5.40, a characteristic signal for the C-5 hydrogen of the title compound.

EXAMPLE 9

(3'S)-1β-Hydroxymethyl-7α-tetrahydropyran-2-yloxy-6β[3'-tetrahydropyran-2-yloxy-trans-1'-octenyl]bicyclo[3.3.0]octan-3-one A degassed solution of 4.0 g (9.2 mmol) of (3'S)-7α-tetrahydropyran-2-yloxy-6β[3'-tetrahydropyran-2-yloxy-trans-1'-octenyl]bicyclo[3.3.0]octen-3-one and 2.0 g of benzophenone in one liter of methanol is photolyzed (3500 Å lamp) for 3 hr while bubbling argon through the solution. The methanol is removed under reduced pressure and the residue chromatographed on 600 g silica gel with a gradient elution of from 3:1 hexane:ethyl to 100% ethyl acetate to give 3.45 g (80%) of title product as a waxy solid. Crystallization from ether and hexane gives the title compound as a white solid, mp 65°–70° ($R_f$ 0.29 in 20% hexane in ethyl acetate).

NMR (CDCl$_3$; TMS): δ 0.89 (t, J=5 Hz, 3H), 1.07–2.90 (m, 28H), 2.92–4.40 (m including a 2H singlet at 3.50 δ, 9H), 4.69 (bs, 2H), 5.24–5.77 (m, 2H).

Infrared: νmax (mull): 3420, 1730, 1200, 1125, 1110, 1070, 1040, 1020, 970 cm$^{-1}$.

EXAMPLE 10

5(Z)-9β-Hydroxymethyl-6a-carba-prostaglandin I$_2$, methyl ester, 11,15 bis(tetrahydropyranyl ether) and 5(E)-9β-hydroxymethyl-6a-carba-prostaglandin I$_2$, methyl ester, 11,15 bis(tetrahydropyranyl ether)

A degassed suspension of 3.53 g (94 mmol) of a mineral oil dispersion of sodium hydride (which had been washed twice with hexane) in 225 ml of dry dimethyl sulfoxide is heated at 65° for one hr under a nitrogen atmosphere, cooled to 15°, and treated portionwise over 15 min with 18.67 g (42.2 mmol) of 4-carboxybutyltriphenylphosphonium bromide. The resulting red solution is treated with a solution of 2.05 g (4.41 mmol) of (3'S)-1β-hydroxymethyl-7α-tetrahydropyran-2-yloxy-6β[3'-tetrahydropyran-2-yloxy-trans-1'-octenyl]bicyclo[3.3.0]octan-3-one in 50 ml of dry dimethyl sulfoxide and then heated at 35°–40° under a nitrogen atmosphere for 90 hr. The resulting dark colored solution is cooled, treated with 30 ml of water, stirred for 30 min at about 20°, added to 500 ml of a 1:1 solution of brine and ice water, acidified with 1N aqueous HCl, and extracted with three 500 ml portions of ether. The combined ether extracts are washed with five 200 ml portions of water and once with 200 ml brine and are dried over anhydrous magnesium sulfate. The solvents are removed under reduced pressure to give 5.8 g of a red-brown oil.

A degassed solution of the 5.8 g of above crude product in 150 ml of acetonitrile at 11° under a nitrogen atmosphere is treated with 56 ml (320 mmol) of diisopropyl ethyl amine followed by 20 ml (320 mmol) of methyl iodide. The resulting solution is stirred at ambient temperature for 20 hr, treated with an additional 4 ml of methyl iodide and stirred for 2 more hr, added to 500 ml of brine, and extracted with two 500 ml portions of ethyl acetate. The combined ethyl acetate extracts are washed with 250 ml of 0.5M aqueous potassium bisulfate solution, 250 ml of saturated aqueous sodium bicarbonate solution, and 250 ml of brine, and are dried over anhydrous sodium sulfate. The solvents are removed under reduced pressure and the residue filtered through 200 g silica gel eluting with 55:45 ethyl acetate-hexane to give 2.4 g of the title compounds.

Chromatography on of silica gel eluting with 55:45 ethyl acetate-hexane affords 0.59 g (24%) of the (5E) isomer as a colorless oil, 0.97 g (39%) of about a 1:1 mixture of both isomers and 0.52 g (21%) of the (5Z) isomer as a colorless oil.

Physical properties for the (5Z) isomer: $R_f$ 0.25 on 60:40 ethyl acetate-hexane.

NMR (CDCl$_3$; TMS): δ 0.89 (t, J=5 Hz, 3H), 1.07–2.80 (m, 35H), 3.2–4.33 (m including 3H singlet at 3.66 δ and 2H singlet at 3.39 δ, 11H), 4.64 (bs, 2H), 5.0–5.8 (m, 3H).

Infrared: νmax (film): 3475 (broad), 1740, 1200, 1120, 1035, 1020, 980 cm$^{-1}$.

Physical properties for the (5E) isomer: $R_f$ 0.29 in 60.40 ethyl acetate-hexane.

NMR (CDCl$_3$; TMS): δ 0.89 (t, J=5 Hz, 3H), 1.07–2.85 (m, 35H), 3.2–4.35 (m including 3H singlet at 3.65 δ and 2H singlet at 3.36 δ, 11H), 4.71 (bs, 2H), 5.0–5.8 (m, 3H).

Infrared: νmax (film): 3475 (broad), 1740, 1200, 1120, 1035, 1020, 980 cm$^{-1}$.

EXAMPLE 11

5(Z)-9β-Hydroxymethyl-6a-carba-prostaglandin I$_2$, methyl ester

A solution of 206 mg (0.37 mmol) of 5(Z)-9β-hydroxymethyl-6a-carba-prostaglandin I$_2$, methyl ester, 11,15 bis(tetrahydropyranyl ether) in 11 ml of 6:3:2 acetic acid-water-tetrahydrofuran is heated at 45° for 3 hr under an inert atmosphere, cooled, diluted with 75 ml brine, and extracted with two 75 ml portions of ethyl acetate. The combined ethyl acetate extracts are washed with three 75 ml portions of saturated aqueous sodium bicarbonate solution, twice with 75 ml brine, and are dried over anhydrous sodium sulfate. The solvents are removed under reduced pressure to give 0.16 g of a yellow oil which was chromatographed on silica gel eluting with 25% acetone in ethyl acetate to give 0.11 g (76%) of the title compound as a colorless oil ($R_f$ 0.22 in 25% acetone in methylene chloride).

NMR (CDCl$_3$; TMS): δ 0.90 (t, J=5 Hz, 3H), 1.07–2.8 (m, 22H), 3.0–4.3 (m including 3H singlet at 3.66 δ and 2H singlet at 3.36 δ, 10H), 5.0–5.8 (m, 3H).

Infrared: νmax (film): 3360 (broad), 1740, 1445, 1440, 1250, 1200, 1170, 1035, 970 cm$^{-1}$.

EXAMPLE 12

5(E)-9β-Hydroxymethyl-6a-carba-prostaglandin I$_2$, methyl ester

A solution of 286 mg (0.508 mmol) of 5(E)-9β-hydroxymethyl-6a-carba-prostaglandin I$_2$, methyl ester, 11,15 bis(tetrahydropyranyl ether) in a solution of 2.7 ml of tetrahydrofuran, 4 ml of water, and 8 ml of acetic acid is heated at 45° under a nitrogen atmosphere for 3 hr, cooled, diluted with 75 ml of brine, and extracted with three 60 ml portions of ethyl acetate. The combined ethyl acetate extracts are washed three times with 75 ml portions of saturated aqueous sodium bicarbonate and twice with 75 ml portions of brine and are dried over anhydrous sodium sulfate. The solvents are removed under reduced pressure to give a yellow oil which is chromatographed on silica gel eluting with 25% acetone in ethyl acetate to give 0.17 g (85%) of the title compound as a colorless oil ($R_f$ 0.22 in 25% EtOAc in hexane).

NMR (CDCl$_3$; TMS): δ 0.90 (t, J=5 Hz, 3H), 1.08–2.8 (m, 22H), 3.0–4.4 (m including 3H singlet at 3.66 δ and 2H singlet at 3.34 δ, 10H), 5.0–5.8 (m, 3H).

Infrared: νmax (film): 3360 (broad), 1740, 1455, 1440, 1250, 1200, 1170, 1135, 1070, 1050, 970 cm$^{-1}$.

EXAMPLE 13

When in the procedure of Example 9 (3'S)-7α-tetrahydropyran-2-yloxy-6β-[3'-tetrahydro-2-yloxyoctanyl]bicyclo[3.3.0]octen-3-one or (3'S)-7α-tetrahydropyran-2-yloxy-6β-[3'-tetrahydro-2-yloxy-1'-octynyl]-bicyclo[3.3.0]octen-3-one is substituted for 3'S)-7α-tetrahydropyran-2-yloxy-6β-[3'-tetrahydropyran-2-yloxy-trans-1'-octenyl]bicyclo[3.3.0]octen-3-one and the general procedure of Example 9 is otherwise followed one obtains respectively (3'S)-1β-hydroxymethyl-7α-tetrahydropyran-2-yloxy-6β-[3'-tetrahydropyran-2-yloxyoctanyl]bicyclo[3.3.0]octan-3-one and (3'S)-1β-hydroxymethyl-7α-tetrahydropyran-2-yloxy-6β-[3'-tetrahydropyran-2-yloxy-1'-octynyl]bicyclo[3.3.0]octan-3-one and when each of these compounds so obtained is substituted for (3'S)-1β-hydroxymethyl-7α-tetrahydropyran-2-yloxy-6β-[3'-tetrahydropyran-2-yloxy-trans-1'-octenyl]bicyclo[3.3.0]octan-3-one in the procedure of Example 10 one obtains respectively the 5E and 5Z isomers of 9β-hydroxymethyl-13,14-dihydro-6a-carba-prostaglandin I$_2$ methyl ester, 11,15-bis(tetrahydropyranyl ether) and 9β-hydroxymethyl-13,14-didehydro-6a-carba-prostaglandin I$_2$ methyl ester, 11,15-bis(tetrahydropyranyl ether).

When the above-obtained 5E and 5Z isomers are each substituted for (5Z)-9β-hydroxymethyl-6a-carba-prostaglandin I$_2$ methyl ester, 11,15-bis(tetrahydropyranyl ether) in Example 11 and the general procedure of Example 11 is followed one obtains the 5E and 5Z individual isomers of 9β-hydroxymethyl-13,14-dihydro-6a-carba-prostaglandin I$_2$ methyl ester and the 5E and 5Z individual isomers of 9β-hydroxymethyl-13,14-didehydro-6a-carba-prostaglandin I$_2$ methyl ester.

EXAMPLE 14

12β-(t-Butyldimethylsilyloxymethyl)-9β-hydroxymethyl-13,14,15,16,17,18,19,20-octanor-6a-carba-prostaglandin I$_2$ A suspnsion of 1.8 g (38 mmol) of sodium hydride (50% in mineral oil) is washed twice with hexane, diluted with 130 ml dry dimethyl sulfoxide, heated at 65° for 50 minutes, cooled to 15°, treated over seven minutes with 9.15 g (21 mmol) of 4-carboxybutyltriphenylphosphonium bromide, stirred at 15°–20° for 15 minutes, treated with 1.49 g (3.2 mmol) 6β-(t-butyldimethylsilyloxymethyl)-7α-(tetrahydropyran-2-yloxy]-1β-(hydroxymethyl)-bicyclo[3.3.0]octan-3-one (using 30 ml of dimethylsulfoxide for the transfer), heated at 40° under a nitrogen atmosphere for 65 hours, cooled to 0°, treated with 15 ml of water, stirred for 2½ hours, diluted with 200 ml of 1:1 brine-ice water, acidified with 30 ml of 1N aqueous hydrochloric acid, and extracted with three 200 ml portions of ether. The combined ether extracts are washed with two 200 ml portions and water and 200 ml of brine and are dried over anhydrous magnesium sulfate. The solvents are removed under reduced pressure and the residue chromatographed on 600 g of acid-washed silica gel eluting with two liters of 5% ethyl acetate in hexane, then 2 liters of 10% ethyl acetate in hexane, then 2 liters of 20% ethyl acetate in hexane, 1 liter of 30% ethyl acetate in hexane, 3 liters of 50% ethyl acetate in hexane, and then 80% ethyl acetate in hexane to give the title product.

EXAMPLE 15

(a) (5Z)-9β-Hydroxymethyl-12β-hydroxymethyl-13,14,15,16,17,18,19,20-octanor-6a-prostaglandin I$_2$, 11 (tetrahydropyranyl ether) and (b) (5E)-9β-Hydroxymethyl-12β-hydroxymethyl-13,14,15,16,17,18,19,20-octanor-6a-carba-prostaglandin I$_2$, 11-(tetrahydropyranyl ether)

A degassed solution of 0.39 g (0.82 mmol) of the compound 29(a) from Example 14 from the previous experiment in 10 ml of dry THF at 0° under an argon atmosphere is treated with 3.0 ml (2.2 mmol) of 0.75M tetra-n-butylammonium fluoride in THF and allowed to warm to room temperature. After 18 hours the solution is added to 50 ml of brine and extracted with three 50 ml portions of ethyl acetate. The combined ethyl acetate extracts are washed with 50 ml of brine and dried over anhydrous sodium sulfate. The solvents are removed under reduced pressure and the residue filtered through 20 g of acid-washed silica gel eluting with 100 ml of 2:1 ethyl acetate-hexane. The resulting yellow oil (upon evaporation of solvents) chromatographed on silica gel eluting with 50:50:0.25 ethyl acetate-hexane-acetic acid to give the title compounds.

EXAMPLE 16

(5Z)-Hydroxymethyl-12β-formyl-13,14,15,16,17,18,19,20-octanor-6a-carba-prostaglandin I$_2$, methyl ester, 11-(tetrahydropyranyl ether)

A solution of 0.30 g (0.83 mmol) of compound 15(a) from Example 15 in 4.3 ml of acetonitrile stirring at ambient temperature under nitrogen is treated with 0.43 ml (2.5 mmol) of diisopropyl ethyl amine and then with 0.26 ml (4.2 mmol) of methyl iodide, stirred in the dark under a nitrogen atmosphere for 25 hours, diluted with 200 ml of ether, and washed with 15 ml of 10% aqueous sodium thiosulfate solution and two 15 ml portions of brine, and dried over anhydrous sodium sulfate. The solvents are removed in vacuo to give 0.31 g of the methyl ester of compound 15(a). Without further purification 287 mg (0.76 mmol) of the above obtained crude oil in 10 ml of methylene chloride at ambient temperature under a nitrogen atmosphere was treated with three spatulas of celite and then all at once with 15 ml of Collins reagent (prepared from 1.55 g of chromium trioxide in 50 ml of methylene chloride treated with 2.5 ml of pyridine and stirred at room temperature under nitrogen for 30 minutes), stirred at ambient temperature for 35 minutes, and filtered through 20 g of silica gel eluting with 100 ml of ethyl acetate. The solvents were removed under reduced pressure and the residue chromatographed on silica gel eluting with 20% ethyl acetate in hexane to give the title compound.

EXAMPLE 17

(5Z)-9β-Hydroxymethyl-15-deoxy-15-keto-16-methyl-18,19-tetradehydro-6a-carba-prostaglandin I$_2$, methyl ester, 11-(tetrahydropyranyl ether)

A mineral oil suspension of sodium hydride (32 mg, 0.7 mmol) in 3 ml of dry THF at 0° under an inert atmosphere is treated with 177 mg (0.76 mmol) of dimethyl-2-oxo-3-methyl-5-heptynyl phosphonate in 4 ml of THF, stirred at 0° for 5 minutes and at room temperature for one hour, cooled to 0° and treated with 239 mg (0.64 mmol) of the compound of Example 16 in 15 ml of THF, stirred at room temperature for 2.5 hours, then diluted with 70 ml of water containing 3 drops of acetic acid, and extracted with three 70 ml portions of ethyl acetate. The combined ethyl acetate extracts are washed with 50 ml of bicarb, 50 ml of brine, and then 25 ml of brine, and are dried over anhydrous sodium sulfate. The solvents are removed under pressure and the residue chromatographed on silica gel eluting with 5:1 hexane-ethyl acetate to give 100 mg of the title compound.

EXAMPLE 18

(5Z)-9β-Hydroxymethyl-16-methyl-18,19-tetradehydro-6a-carba-prostaglandin $I_2$, methyl ester A solution of 20.3 mg (0.54 mmol) sodium borohydride in 3 ml of methanol at −25° under an argon atmosphere is treated with 99 mg (0.21 mmol) of the compound of Example 17 and 0.2 ml methylene chloride dropwise using 2 ml of methanol for the transfer. The resulting solution is stirred one hour at −25° to −15°, quenched with 0.2 ml of acetic acid, added to 40 ml of brine, and extracted with three 50 ml portions of ethyl acetate. The combined ethyl acetate extracts are washed with 40 ml of bicarb and then 40 ml of brine and are dried over anhydrous sodium sulfate. The solvents are removed under reduced pressure and the residue chromatographed on silica gel eluting with 2:1 hexane-ethyl acetate to give an alcohol mixture.

Without further purification the alcohol mixture is dissolved in 1.5 ml of THF, 2.3 ml of water, and 4.5 ml of glacial acetic acid, and heated at 40°–45° under a nitrogen atmosphere for three hours, cooled, diluted with 50 ml of brine, and extracted with two 50 ml portions of ethyl acetate. The combined ethyl acetate extracts are washed with 50 ml of brine, three 50 ml portions of bicarb, and 50 ml of brine, and dried over anhydrous sodium sulfate. The solvents are removed in vacuo and the residue chromatographed on 20 g of silica gel eluting with 80 ml 20% acetone in methylene chloride then with 30% acetone in methylene chloride to give the 15β-isomer of the title compound.

EXAMPLE 19

When in the procedure of Example 17 each of the following phosphonates is substituted for dimethyl-2-oxo-3-methyl-5-heptynyl phosphonate and the procedures of Examples 17 and 18 are followed one obtains the 9β-ethynyl products listed below:
dimethyl-2-oxo-3-phenylpropyl phosphonate;
dimethyl-2-oxo-4-phenylbutyl phosphonate;
dimethyl-2-oxo-3-phenoxypropyl phosphonate;
dimethyl-2-oxo-4-(3-thienyl)butyl phosphonate;
dimethyl-2-cyclohexyl-2-oxoethyl phosphonate;
dimethyl-2-oxo-3-(3-thienyloxy)propyl phosphonate; or dimethyl-2-oxo-2-(3-ethylcyclobutyl)ethyl phosphonate;
(5Z)-9β-hydroxymethyl-16-phenyl-17,18,19,20-tetranor-6a-carba-prostaglandin $I_2$, methyl ester;
(5Z)-9β-hydroxymethyl-17-phenyl-18,19,20-trinor-6a-carba-prostaglandin $I_2$, methyl ester;
(5Z)-9β-hydroxymethyl-16-phenoxy-17,18,19,20-tetranor-6a-carba-prostaglandin $I_2$, methyl ester;
(5Z)-9β-hydroxymethyl-17-(3-thienyl)-18,19,20-trinor-6a-carba-prostaglandin $I_2$, methyl ester;
(5Z)-9β-hydroxymethyl-15-cyclohexyl-16,17,18,19,20-pentanor-6a-carba-prostaglandin $I_2$, methyl ester;
(5Z)-9β-hydroxymethyl-16-(3-thienyloxy)-17,18,19,20-tetranor-6a-carba-prostaglandin $I_2$, methyl ester; and
(5Z)-9β-hydroxymethyl-15-(3-ethylcyclobutyl)-16,17,18,19,20-pentanor-6a-carba-prostaglandin $I_2$, methyl ester.

EXAMPLE 20

When each of the 9β-hydroxymethyl derivatives obtained in Example 19 is substituted for (5E,5Z)-9β-hydroxymethyl-6a-carba-prostaglandin $I_2$ methyl ester in the procedure of Example 1 the following compounds are obtained.
(5Z)-9β-carboxy-16-phenyl-17,18,19,20-tetranor-6a-carba-prostaglandin $I_2$, methyl ester;
(5Z)-9β-carboxy-17-phenyl-18,19,20-trinor-6a-carba-prostaglandin $I_2$, methyl ester;
(5Z)-9β-carboxy-16-phenoxy-17,18,19,20-tetranor-6a-carba-prostaglandin $I_2$, methyl ester;
(5Z)-9β-carboxy-17-(3-thienyl)-18,19,20-trinor-6a-carba-prostaglandin $I_2$, methyl ester;
(5Z)-9β-carboxy-15-cyclohexyl-16,17,18,19,20-pentanor-6a-carba-prostaglandin $I_2$, methyl ester;
(5Z)-9β-carboxy-16-(3-thienyloxy)-17,18,19,20-tetranor-6a-carba-prostaglandin $I_2$, methyl ester; and
(5Z)-9β-carboxy-15-(3-ethylcyclobutyl)-16,17,18,19,20-pentanor-6a-carba-prostaglandin $I_2$, methyl ester.

EXAMPLE 21

When each of the 9β-carboxyderivatives obtained in Example 20 is treated with 2,3-dihydropyran as generally described herein to protect the 11- and 15-position hydroxyl groups and then is substituted for (5E,5Z)-9β-carboxy-6a-carba-prostaglandin $I_2$ methyl ester, 11,15-bis(tetrahydropyranyl ether) in the procedure of Example 2 and the procedures of Examples 2 and 3 are followed the following compounds are obtained:
(5Z)-9β-chloro-16-phenyl-17,18,19,20-tetranor-6a-carba-prostaglandin $I_2$;
(5Z)-9β-chloro-17-phenyl-18,19,20-trinor-6a-carba-prostaglandin $I_2$;
(5Z)-9β-chloro-16-phenoxy-17,18,19,20-tetranor-6a-carba-prostaglandin $I_2$;
(5Z)-9β-chloro-17-(3-thienyl)-18,19,20-trinor-6a-carba-prostaglandin $I_2$;
(5Z)-9β-chloro-15-cyclohexyl-16,17,18,19,20-pentanor-6a-carba-prostaglandin $I_2$;
(5Z)-9β-chloro-16-(3-thienyloxy)-17,18,19,20-tetranor-6a-carba-prostaglandin $I_2$; and
(5Z)-9β-chloro-15-(3-ethylcyclobutyl)-16,17,18,19,20-pentanor-6a-carba-prostaglandin $I_2$.

FORMULA CHART

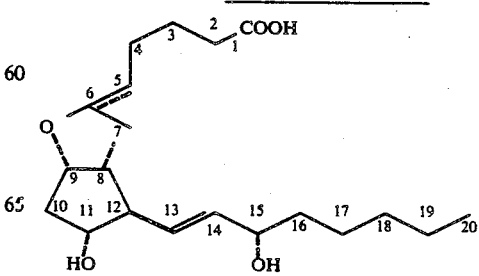

I

-continued
FORMULA CHART
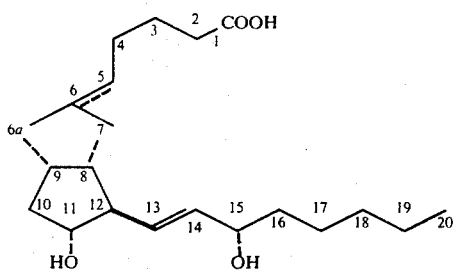
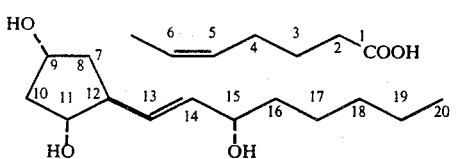
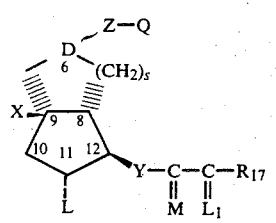
Formula IV
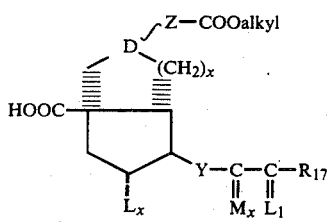
Formula V
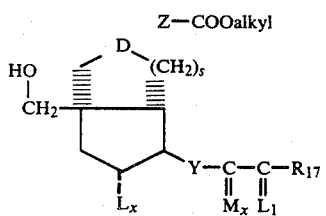
Formula VI
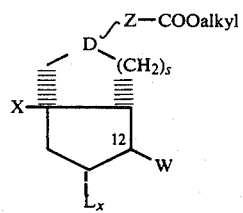
Formula VII
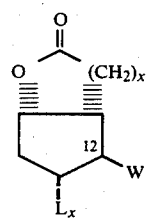
Formula VIII
-continued
FORMULA CHART
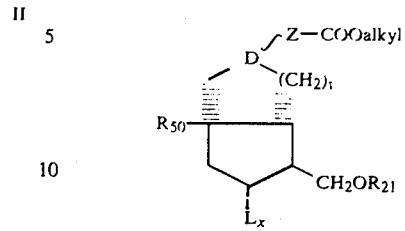
| Formula | $R_{50}$ |
|---|---|
| IX | Cl, I, or $CF_3$ |
| X | —COOH |
| XI | —$CH_2OH$ |
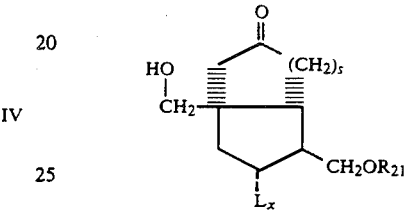
Formula XII
CHART A
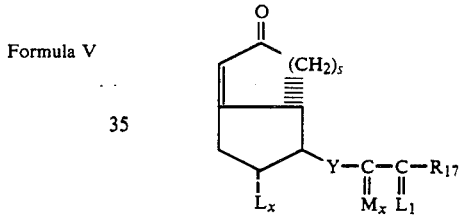
Formula A-1
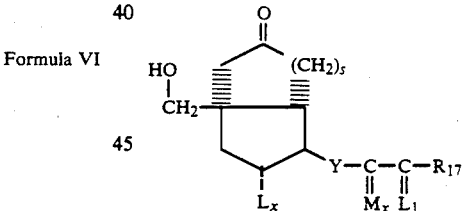
Formula A-2
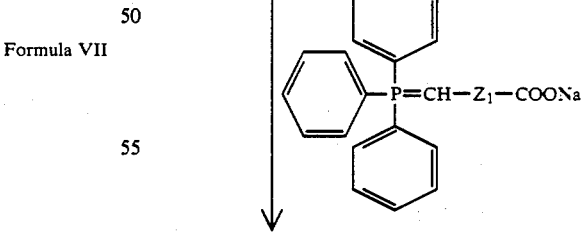
Formula A-3
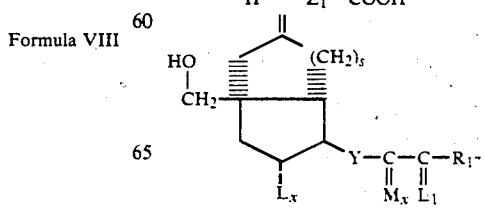
Formula A-4

CHART B
Formula A-2 →
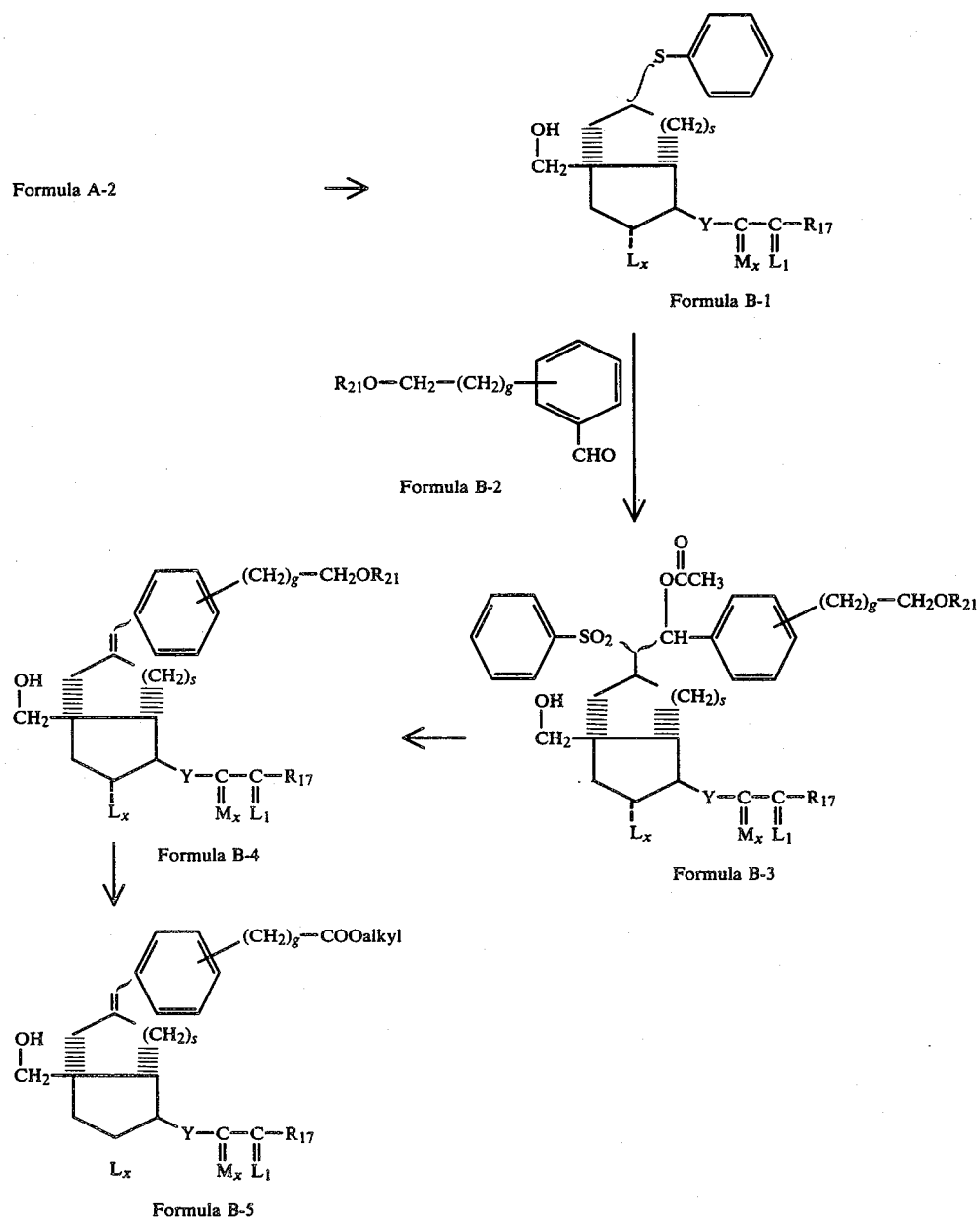
CHART C
Formula A-2 and Formula A-3 +
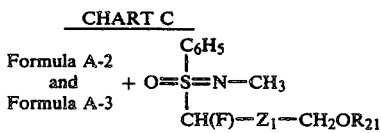
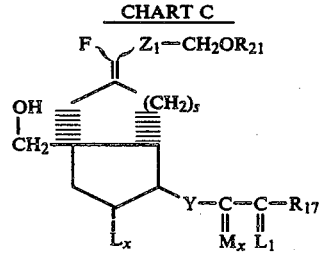

-continued
CHART C

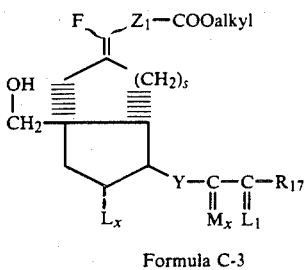

Formula C-3

I claim:
1. A compound of the formula

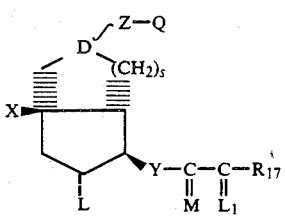

wherein X is chloro, iodo, trifluoromethyl, or —COOH;
wherein D is cis—C=C($R_3$)—, trans—C=C($R_3$)— or >CHCH$_2$, wherein $R_3$ is hydrogen or fluoro;
wherein Z is:
(1) —CH$_2$—(CH$_2$)$_f$—C($R_4$)$_2$— wherein each $R_4$ is the same and is hydrogen or fluoro, and f is zero, one, 2 or 3;
(2) trans—CH$_2$—CH=CH—; or
(3) —(Ph)—(CH$_2$)$_g$— wherein Ph is 1,2-, 1,3-, or 1,4-phenylene and g is zero, one, 2 or 3; with the proviso that when Z is —(Ph)—(CH$_2$)$_g$—, $R_3$ is hydrogen;
wherein Q is
(1) —COOR$_5$, wherein $R_5$ is
  (a) hydrogen,
  (b) (C$_1$-C$_{12}$)alkyl,
  (c) (C$_3$-C$_{10}$)cycloalkyl,
  (d) (C$_7$-C$_{12}$)aralkyl,
  (e) phenyl optionally substituted with one, 2 or 3 chloro or (C$_1$-C$_4$)alkyl,
  (f) phenyl substituted in the para-position with —NHCOR$_6$, —COR$_7$, —OC(O)R$_8$ or —CH=N—NHCONH$_2$, wherein $R_6$ is methyl, phenyl, acetamidophenyl, benzamidophenyl or —NH$_2$; $R_7$ is methyl, phenyl, —NH$_2$, or methoxy; and $R_8$ is phenyl or acetamidophenyl;
  (g) phthalidyl,
  (h) 3-(5,5-dimethyl-1,3,2-dioxaphosphorinan-2-yl)-2-oxopropan-1-yl P-oxide.
  (i) 3-(5,5-di(hydroxymethyl)-1,3,2-dioxaphosphorinan-2-yl)-2-oxopropan-1-yl P-oxide, or
  (j) a pharmacologically acceptable cation; with the proviso that when X is —COOH, Q is —COOR$_5$ wherein $R_5$ is (C$_{1-4}$alkyl);
(2) —CH$_2$OH;
(3) —COL$_2$, wherein L$_2$ is
  (a) an amino group of the formula —NR$_9$R$_{10}$ wherein R$_9$ is hydrogen or (C$_1$-C$_{12}$)alkyl and $R_{10}$ is
    (i) hydrogen
    (ii) (C$_1$-C$_{12}$)alkyl
    (iii) (C$_3$-C$_{10}$)cycloalkyl,
    (iv) (C$_7$-C$_{12}$)aralkyl
    (v) phenyl optionally substituted with one, 2 or 3 chloro, (C$_1$-C$_3$)alkyl, hydroxy, carboxy, (C$_2$-C$_5$)alkoxycarbonyl, or nitro,
    (vi) (C$_2$-C$_5$)carboxyalkyl,
    (vii) (C$_2$-C$_5$)carbamoylalkyl,
    (viii) (C$_2$-C$_5$)cyanoalkyl,
    (ix) (C$_3$-C$_6$)acetylalkyl,
    (x) (C$_7$-C$_{12}$)benzoalkyl, optionally substituted by one, 2, or 3 chloro, (C$_1$-C$_3$)alkyl, hydroxy, (C$_1$-C$_3$)alkoxy, carboxy, (C$_2$-C$_5$)-alkoxycarbonyl, or nitro,
    (xi) pyridyl, optionally substituted by one, 2, or 3 chloro (C$_1$-C$_3$)alkyl, or (C$_1$-C$_3$)alkoxy,
    (xii) (C$_6$-C$_9$)pyridylalkyl optionally substituted by one, 2, or 3 chloro, (C$_1$-C$_3$)alkyl, hydroxy, or (C$_1$-C$_3$)alkyl,
    (xiii) (C$_1$-C$_4$)hydroxyalkyl,
    (xiv) (C$_1$-C$_4$)dihydroxyalkyl,
    (xv) (C$_1$-C$_4$)trihydroxyalkyl;
  (b) cycloamine selected from the group consisting of pyrolidino, piperidino, morpholino, piperazino, hexamethyleneimino, pyrroline, or 3,4-didehydropiperidinyl optionally substituted by one or 2 (C$_1$-C$_{12}$)alkyl;
  (c) carbonylamino of the formula —NR$_{11}$COR$_{10}$, wherein R$_{11}$ is hydrogen or (C$_1$-C$_4$)alkyl and R$_{10}$ is other than hydrogen, but otherwise defined as above;
  (d) sulfonylamino of the formula —NR$_{11}$SO$_2$R$_{10}$, wherein R$_{11}$ and R$_{10}$ are defined in (c);
(4) —CH$_2$NL$_3$L$_4$, wherein L$_3$ and L$_4$ are hydrogen or (C$_1$-C$_4$)alkyl, being the same or different, or the pharmacologically acceptable acid addition salts thereof when Q is —CH$_2$NL$_3$L$_4$; or
(5) —CN;
wherein s is the integer one or 2;
wherein L is H,H; α-OR$_{12}$,β-H; α-H,β-OR$_{12}$; α-CH$_2$OR$_{12}$,β-H; α-H,β-CH$_2$OR$_{12}$
wherein R$_{12}$ is hydrogen or a hydroxyl protective group with the proviso that when X is —COOH, R$_{12}$ is other than hydrogen;
wherein Y is trans —CH=CH—, cis—CH=CH—, —CH$_2$CH$_2$—, or —C≡C—;
wherein M is α-OR$_{12}$,β-R$_{14}$; or α-R$_{14}$,β-OR$_{12}$, wherein R$_{12}$ is as defined above, and R$_{14}$ is hydrogen or methyl;
wherein L$_1$ is α-R$_{15}$,β-R$_{16}$; α-R$_{16}$,β-R$_{15}$; or a mixture thereof wherein R$_{15}$ and R$_{16}$ are hydrogen, methyl, or fluoro being the same or different with the proviso that one of R$_{15}$ and R$_{16}$ is fluoro only when the other of R$_{15}$ and R$_{16}$ is hydrogen or fluoro;
wherein R$_{17}$ is
(1) —C$_m$H$_{2m}$CH$_3$ wherein M is an integer of from one to 5,
(2) phenoxy optionally substituted by one, 2, or 3 chloro, fluoro, trifluoromethyl, (C$_1$-C$_3$)alkyl, or (C$_1$-C$_3$)alkoxy, with the proviso that not more than two substituents are other than alkyl and with the proviso that R$_{17}$ is phenoxy or substituted phenoxy, only when R$_{15}$ and R$_{16}$ are hydrogen or methyl, being the same or different;
(3) phenyl, benzyl, phenylethyl, or phenylpropyl optionally substituted on the aromatic ring by one, 2, or 3 chloro, fluoro, trifluoromethyl (C$_1$-C$_3$)alkyl, or ($C_1$-$C_3$)alkoxy, with the proviso that not more than two substituents are other than alkyl, (4) cis—CH=CH—$CH_2CH_3$, (5) —$(CH_2)_2$—CH(OH)—$CH_3$, (6) —$(CH_2)_3$—CH=C($CH_3$)$_2$,

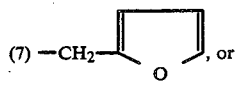

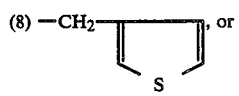

wherein $-\underset{\underset{L_1}{\|}}{C}-R_{17}$ taken together is (1) ($C_4$-$C_7$)cycloalkyl optionally substituted by one to 3 ($C_1$-$C_5$)-alkyl, (2) 3-thienyloxymethyl,

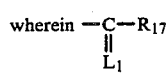

(4) —C≡C—$C_qH_{2q}CH_3$ wherein q is an integer of from 2 to 6, or (5) —$C_pH_{2p}$CH=$CH_2$ wherein p is an integer of from 3 to 7;

and individual optical isomers thereof.

2. A compound of claim 1 wherein $R_{12}$ is hydrogen or a pharmacologically acceptable salt thereof.

3. A compound of claim 2 wherein s is one and D is cis—C=C($R_3$)— or trans—C=C($R_3$)—.

4. A compound of claim 3 wherein $R_3$ is hydrogen.

5. A compound of claim 3 or 4 wherein Y is trans—CH=CH—, —C≡C— or —$CH_2CH_2$—.

6. A compound of claim 5 wherein Q is —$COOR_5$ or $COL_2$ wherein $L_2$ is an amine group of the formula —$NR_9R_{10}$.

7. A compound of claim 6 wherein $R_{17}$ is —$C_mH_{2m}CH_3$ wherein m is an integer of from one to 5; phenoxy; phenyl; benzyl; or 3-thienylmethyl; or wherein

taken together is cyclohexyl; 3-ethylcyclobutyl; 3-thienyloxymethyl; or

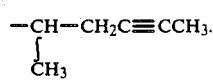

8. A compound of claim 7 wherein $R_5$ is hydrogen, a pharmacologically acceptable cation, methyl or ethyl, and $R_{17}$ is —$C_mH_{2m}CH_3$ wherein m is an integer of from one to 5 carbon atoms or wherein

taken together is $-\underset{\underset{CH_3}{|}}{CH}-CH_2C{\equiv}CCH_3$.

9. A compound of claim 3 or 8 wherein X is chloro.

10. A compound of claim 9 which is the 5Z isomer.

11. A compound of claim 9 which is (5Z)-9β-chloro-6a-carba-prostaglandin $I_2$.

12. A compound of claim 8 which is (5Z)-9β-iodo-6a-carba-prostaglandin $I_2$.

* * * * *